United States Patent
Walder et al.

(10) Patent No.: US 11,260,129 B2
(45) Date of Patent: Mar. 1, 2022

(54) PHOSPHOR-CONTAINING DRUG ACTIVATOR, SUSPENSION THEREOF, SYSTEM CONTAINING THE SUSPENSION, AND METHODS FOR USE

(71) Applicants: IMMUNOLIGHT, LLC, Detroit, MI (US); DUKE UNIVERSITY, Durham, NC (US)

(72) Inventors: Harold Walder, Belville, NC (US); Frederic A. Bourke, Jr., Aspen, CO (US); Zakaryae Fathi, Raleigh, NC (US); Wayne Beyer, Bahama, NC (US); Mark Oldham, Durham, NC (US); Justus Adamson, Durham, NC (US); Michael Nolan, Raleigh, NC (US)

(73) Assignees: IMMUNOLIGHT, LLC, Detroit, MI (US); DUKE UNIVERSITY, Durham, NC (US)

( * ) Notice: Subject to any disclaimer, the term of this patent is extended or adjusted under 35 U.S.C. 154(b) by 308 days.

(21) Appl. No.: 16/074,707

(22) PCT Filed: Feb. 2, 2017

(86) PCT No.: PCT/US2017/016138
§ 371 (c)(1),
(2) Date: Aug. 1, 2018

(87) PCT Pub. No.: WO2017/013650
PCT Pub. Date: Aug. 10, 2017

(65) Prior Publication Data
US 2020/0282056 A1 Sep. 10, 2020

Related U.S. Application Data

(60) Provisional application No. 62/290,203, filed on Feb. 2, 2016, provisional application No. 62/304,525, filed on Mar. 7, 2016.

(51) Int. Cl.
A61K 9/00 (2006.01)
A61K 41/00 (2020.01)
(Continued)

(52) U.S. Cl.
CPC .......... *A61K 41/0066* (2013.01); *A61K 31/37* (2013.01); *A61N 5/062* (2013.01);
(Continued)

(58) Field of Classification Search
CPC ..................................... A61K 41/66
See application file for complete search history.

(56) References Cited

U.S. PATENT DOCUMENTS 5,820,872 A 10/1998 Edelson et al.
2009/0104130 A1 4/2009 Bernstein et al.
(Continued)

FOREIGN PATENT DOCUMENTS

WO WO 00/47402 A1 8/2000
WO WO 00/48402 A1 8/2000
(Continued)

OTHER PUBLICATIONS

Japanese Office Action dated Feb. 1, 2021 in Japanese Patent Application No. 2018-559681 (with English translation), 8 pages.
(Continued)

*Primary Examiner* — Paul W Dickinson
(74) *Attorney, Agent, or Firm* — Oblon, McClelland, Maier & Neustadt, L.L.P.

(57) ABSTRACT

A phosphor-containing drug activator and suspension thereof are provided. The suspension at least includes two or more phosphors capable of emitting ultraviolet and visible light upon interaction with x-rays. The two or more phosphors include Zn2SiO4:M12+ and (3Ca3 (PO4)2Ca(F, Cl)2: Sb3*, Mn2+) at a ratio NP-200:GTP-4300 of from 1:10 to 10:1, and each of the two phosphors have an ethylene
(Continued)

cellulose coating and/or a diamond-like carbon coating. The suspension further includes a pharmaceutically acceptable carrier. A system for treating a disease in a subject in need thereof includes a) the above-noted suspension, b) a photoactivatable drug containing 8-methoxypsoralen (8-MOP or UVADEX) untethered from the two or more phosphors, c) one or more devices which infuse the photoactivatable drug and the suspension including the pharmaceutically acceptable carrier into a diseased site in the subject, and d) an x-ray source which is controlled to deliver a dose of x-rays to the subject for production of the ultraviolet light.

91 Claims, 21 Drawing Sheets

(51) Int. Cl.
    *A61K 31/37*     (2006.01)
    *A61N 5/06*     (2006.01)
    *A61N 5/10*     (2006.01)
    A61K 45/06     (2006.01)

(52) U.S. Cl.
    CPC ............... *A61N 5/10* (2013.01); *A61K 45/06* (2013.01); *A61N 2005/0661* (2013.01); *A61N 2005/1098* (2013.01)

(56) References Cited

U.S. PATENT DOCUMENTS

| | | |
|---|---|---|
| 2013/0189803 A1 | 7/2013 | Nasaani et al. |
| 2019/0022221 A1 | 1/2019 | Bourke et al. |

FOREIGN PATENT DOCUMENTS

| | | |
|---|---|---|
| WO | WO 2008/130562 A1 | 10/2008 |
| WO | WO 2014/143826 A2 | 9/2014 |
| WO | WO 2015/164485 A1 | 10/2015 |
| WO | WO 2016/115225 A1 | 7/2016 |

OTHER PUBLICATIONS

International Preliminary Report on Patentability and Written Opinion dated Aug. 16, 2018in PCT/US2017/016138 (English Translation only), 17 pages.
Indian Office Action dated Aug. 13. 2020 in Indian Patent Application No. 201817031969 (with English translation), 6 pages.
European Communication pursuant to Rules 70(2) and 70a(2) EPC dated Jan. 3, 2020 in corresponding European Patent Application No. 17748119.9, 1 page.
Extended European Search Report dated Dec. 4, 2019 in corresponding European Patent Application No. 17748119.9 citing documents AO-AQ therein, 7 pages.
Combined Chinese Office Action and Search Report dated Mar. 4, 2020 in corresponding Chinese Patent Application No. 201780014860.2 (with English Translation of Category of Cited Documents), citing document AO therein, 14 pages.
Office Action dated Oct. 23, 2019 in corresponding Israeli Patent Application No. 260849, 2 pages.
International Search Report dated Apr. 5, 2017, in PCT/US2017/016138 filed Feb. 2, 2017.
Notice of Reasons for Rejection dated Jun. 28, 2021 in Japanese Patent Application No. 2018-559681 (with English language translation), 6 pages.
Australian Office Action dated Aug. 4, 2021 in Australian Patent Application No. 2017213801, 4 pages.

Fit: Annexin V (+) =A +B [Psoralen] + C [Phosphor] = D [Psoralen] [Phosphor]

| Equation Coefficients | Coefficient Estimate | P-value | |
|---|---|---|---|
| A (Intercept) | 3.7E-02 | 0.071 | |
| B (8-MOP effects) | -1.2E-03 | 0.096 | |
| C (phosphor effects) | -5.4E-04 | 0.050 | $R^2$ |
| D (Interaction effects) | 6.8E-05 | <.0001 | 0.718 |

PHOSPHOR-CONTAINING DRUG ACTIVATOR, SUSPENSION THEREOF, SYSTEM CONTAINING THE SUSPENSION, AND METHODS FOR USE

CROSS REFERENCE TO RELATED APPLICATIONS

This application is related to U.S. provisional Ser. No. 61/982,585, filed Apr. 22, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE", the entire contents of which are hereby incorporated by references. This application is related to provisional Ser. No. 62/096,773, filed: Dec. 24, 2014, entitled " INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of each of which is incorporated herein by reference. This application is related to U.S. provisional Ser. No. 62/132,270, filed Mar. 12, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references. This application is related to U.S. provisional Ser. No. 62/147,390, filed Apr. 14, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references.

This application is related to provisional U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to U.S. Ser. No. 13/102,277 entitled "ADHESIIVE BONDING COMPOSITION AND METHOD OF USE," tiled May 6, 2011, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPSI) AND EXCITON-PLASMON ENHANCED PHOTOTHERAPY (EPEP)," the entire contents of which are hereby incorporated herein by reference. This application is related to non-provisional Ser. No. 12/389,946, tiled Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655, filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is also related to provisional Ser. No. 61/792,125, filed Mar. 15, 2013, entitled "INTERIOR ENERGY-ACTIVATION OF PHOTO-REACTIVE SPECIES INSIDE A MEDIUM OR BODY," the entire contents of which are hereby incorporated herein by reference. This application is further related to provisional Ser. No. 61/505,849 filed Jul. 8, 2011, and U.S. application Ser. No. 14/131,564, filed Jan. 8, 2014, each entitled "PHOSPHORS AND SCINTILLATORS FOR LIGHT STIMULATION WITHIN A MEDIUM," the entire contents of each of which is incorporated herein by reference. This application is related to and U.S. application Ser. No. 14/206,337, filed Mar. 12, 2014, entitled "INTERIOR ENERGY-ACTIVATION OF PHOTO-REACTIVE SPECIES INSIDE A MEDIUM OR BODY." the entire contents of which are hereby incorporated herein by reference. This application is related to national stage PCT/US2015/027058 filed Apr. 22, 2015, entitled "TUMOR IMAGING WITH X-RAYS AND OTHER HIGH ENERGY SOURCES USING AS CONTRAST AGENTS PHOTON-EMITTING PHOSPHORUS HAVING THERAPEUTIC PROPERTIES," the entire contents of which are hereby incorporated herein by reference. This application is related U.S. Ser. No. 62/243,465 filed Oct. 19, 2015, entitled "X-RAY PSORALEN ACTIVATED CANCER THERAPY (X-PACT)," the entire contents of which are hereby incorporated herein by reference.

This application is related to and claims priority to U.S. Ser. No. 62/290,203 filed Feb. 2, 2016, entitled "PHOSPHOR-CONTAINING DRUG ACTIVATOR, SUSPENSION THEREOF, SYSTEM CONTAINING THE SUSPENSION, AND METHODS FOR USE" and U.S. Ser. No. 62/304,525 filed Mar. 7, 2016, entitled "PHOSPHOR-CONTAINING DRUG ACTIVATOR, SUSPENSION THEREOF, SYSTEM CONTAINING THE SUSPENSION, AND METHODS FOR USE" (the entire contents of both U.S. provisional applications are incorporated herein by reference).

BACKGROUND OF THE INVENTION

Field of Invention

The invention relates to methods and systems for treating cell proliferation disorders, that provide better distinction between normal, healthy cells and those cells suffering a cell proliferation and preferably that can be performed using non-invasive or minimally invasive techniques.

Discussion of the Background

Light modulation from a deeply penetrating radiation like X-ray opens the possibility for activating bio-therapeutic agents of various kinds within mammalian bodies. As an example, the binding of psoralen to DNA through the formation of monoadducts is well known to engender an immune response if done properly. Psoralen under the correct light activation gains the aptitude to bind to DNA. Psoralen has been reported to react to other sites that have a suitable reactivity including and not limited to cell walls.

If this reaction is of the correct kind, as is the case for psoralen-DNA monoadducts formation, the binding leads to a programmable cell death referred to as Apoptosis. Such programmable cell death, if accomplished over a cell population, can signal the body to mount an immune response permitting target specific cell kill throughout the body. Such immune response is of importance for various medical treatments including cancer treatment.

Psoralens are naturally occurring compounds found in plants (furocoumarin family) with anti-cancer and immunogenic properties. They freely penetrate the phospholipid cellular bilayer membranes and intercalate into DNA between nucleic acid pyrimidines, where they are biologically inert (unless photo-activated) and ultimately excreted within 24 hours. However psoralens are photo-reactive, acquiring potent cytotoxicity after 'activation' by ultraviolet (UVA) light. When photo-activated, psoralens form mono-adducts and di-adducts with DNA leading to marked tumor cytotoxicity and apoptosis. Cell signaling events in response to DNA damage include up-regulation of $p21^{wal/Cip}$ and p53 activation, with mitochondrial induced cytochrome c release and consequent cell death. Photo-activated psoralen can also induce apoptosis by blocking oncogenic receptor tyrosine kinase signaling, and can affect immunogenicity and photochemical modification of a range of cellular proteins in treated cells.

Importantly, psoralen can promote a strong long-term clinical response, as observed in the treatment of cutaneous T Cell Lymphoma utilizing extracorporeal photopheresis (ECP). fir ECP malignant CTCL cells are irradiated with ultraviolet A (UVA) light in the presence of psoralen, and then re-administered to the patient. Remarkably, complete long term responses over many decades have been observed in a sub-set of patients, even though only a small fraction of malignant cells were treated. In addition to ECP, psoralens have also found wide clinical application through PUVA treatment of proliferative skin disorders and cancer including psoriasis, vitiligo, mycosis fungoides, and melanoma.

The cytotoxic and immunogenic effects of psoralen are often attributed to psoralen mediated photoadduct DNA damage. A principle mechanism underlying the long-term immunogenic clinical response likely derives from psoralen induced tumor cell cytotoxicity and uptake of the apoptotic cells by immature dendritic cells, in the presence of inflammatory cytokines. However, photochemical modification of proteins and other cellular components can also impact the antigenicity and potential immunogenicity of treated cells. The diversity and potency of psoralen application is further illustrated by recent success using psoralen in the development of virus vaccines.

SUMMARY OF THE INVENTION

In one embodiment, the present invention provides a phosphor-containing drug activator comprising an admixture of two or more phosphors, which include $Zn_2SiO_4:Mn^{2\circ}$ and $(3Ca_3(PO_4)_2.Ca(F, Cl)_2: Sb^{3+}, Mn^{2+})$ at a ratio from 1:10 to 10:1, wherein each of the two phosphors have at least one coating selected from the group consisting of an ethylene cellulose coating and a diamond-like carbon coating. The admixture is preferably in dry solid/powder form.

In one embodiment, there is provided a suspension of the phosphor-containing drug activator. The suspension at least includes two or more phosphors capable of emitting ultraviolet and visible light upon interaction with x-rays. The two or more phosphors include $Zn_2SiO_4:Mn^{2+}$ and $(3Ca_3(PO_4)_2Ca(F, Cl)_2: Sb^{3+}, Mn^{2+})$ at a ratio from 1:10 to 10:1, and each of the two phosphors have at least one coating selected from the group consisting of an ethylene cellulose coating and a diamond-like carbon coating. The suspension further includes a pharmaceutically acceptable carrier.

In one embodiment, there is provided a system for treating a disease in a subject in need thereof The system includes a) the above-noted suspension, b) a photoactivatable drug comprising 8 MOP or UV ALEX untethered from the two or more phosphors, c) one or more devices which infuse the photoactivatable drug and the suspension including the pharmaceutically acceptable carrier into a diseased site in the subject, and d) an x-ray source which is controlled to deliver a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

In further embodiments, there are provided methods for treating a disease in a subject in need thereof using the phosphor-containing drug activator, either in its dry admixture form or its suspension form. One method includes a) infusing the photoactivatable drug and the suspension including the pharmaceutically acceptable carrier into a diseased site in the subject, and b) delivering a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor. A further method includes a) hydrating the dry admixture of the phosphor-containing drug activator, b) combining the hydrated form of the phosphor-containing drug activator with the photoactivatable drug, with the combining either being subsequent to the hydrating or simultaneously with the hydrating, and c) delivering a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
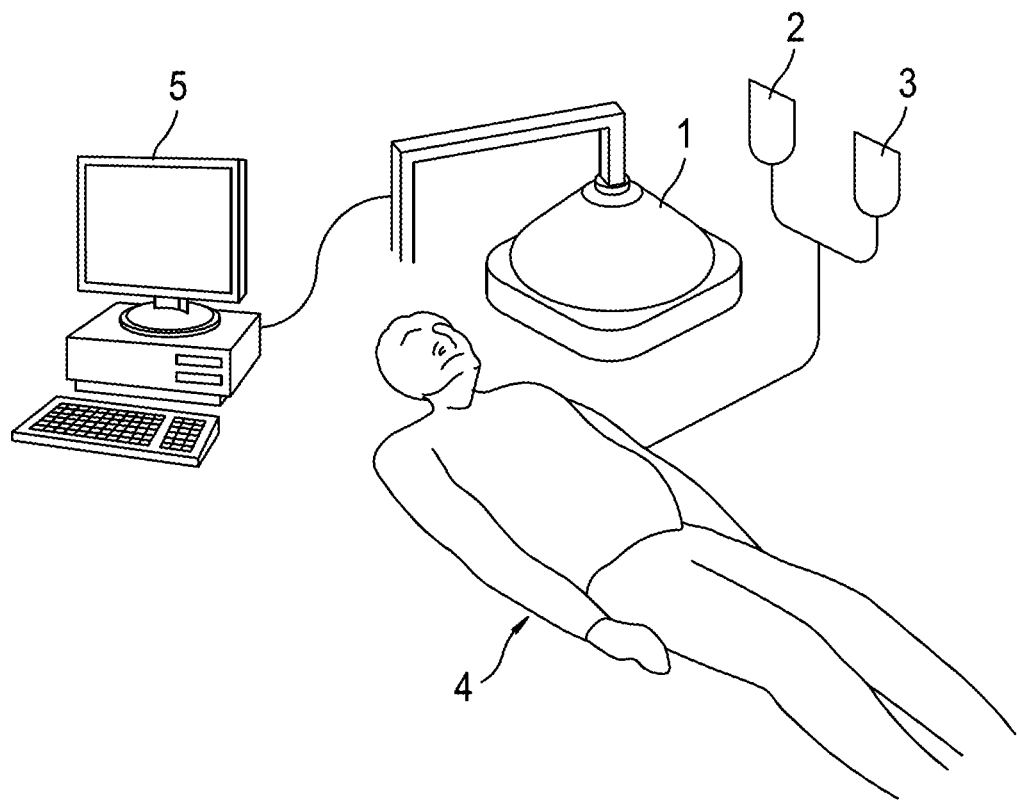
FIG. 1A illustrates a system according to one exemplary embodiment of the present invention.

The present invention sets forth a novel method of treating cell proliferation disorders that is effective, specific, and has few side-effects.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, staphylococcus aureus (particularly antibiotic resistant strains such as methicillin resistant staphylococcus aureus or MRSA), and autoimmune disorders.

Those cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, a photoactivatable agent, such as a psoralen or a psoralen derivative, is exposed in situ an energy source (e.g., x-rays) capable of activating energy modulation agents (e.g., phosphors) which emit light to activate photoactivatable agents such as psoralen or coumarin.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the terms "at" or "about," as used herein when referring to a measurable value or metric is meant to encompass variations of 20%, 10%, 5%, 1%, 0.5%, or even 0.1% of the specified amount, for example a specified ratio, a specified thickness, a specified phosphor size, or a specified water contact angle. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The present invention utilizes x-ray driven activation of 8MOP (or UVADEX) to induce a persistent anti-tumor response and a resulting arrest of tumor growth or regression. As used herein, a persistent antitumor response is a response which slows or stops the tumor growth from that of a control or blind subject receiving only a placebo. The present invention demonstrates that x-ray driven activation of a photoactivatable drug (e.g., 8 MOP) slows tumor growth in some cases and in other cases arrests growth of the tumor leading to signs of complete remission for the subject.

In particular, the present invention utilizes a novel phosphor-containing drug activator for causing a change in activity in a subject that is effective, specific, and able to produce a change to the medium or body. The phosphor-containing drug activator comprises a mixture of two different phosphors, which upon x-ray excitation, each have emissions in the UV and visible spectrum. The mixture of phosphors results in superior performance compared to either phosphor alone. The mixture of phosphors preferably includes a mixture of two or more phosphors, namely NP-200 and GTP-4300, that are purchased from Nichia and Global Tungsten and Powders, respectively. The chemical formulas of these phosphors are $Zn_2SiO_4:Mn^{2+}$ and $(3Ca_3(PO_4)_2Ca(F, Cl)_2: Sb^{3+}, Mn^{2+})$, respectively. These phosphors absorb penetrating forms of energy (e.g., low dose x-rays) and emit light in wavelengths that activate the 8 MOP (or UVADEX) in-situ. In one embodiment of the invention, the phosphors in the novel phosphor-containing drug activator are coated with a biocompatible Ethyl Cellulose coating and/or coated with a Diamond Like Carbon (DLC) coatings. The coatings are described below.

Reference will now be made in detail to the present preferred embodiments of the invention, examples of which are illustrated in the accompanying drawings (including color drawings), in which like reference characters refer to corresponding elements.

FIG. 1A illustrates a system according to one exemplary embodiment of the invention. Referring to FIG. 1A, an exemplary system according to one embodiment of the invention may have an initiation energy source 1 directed at the subject 4. An activatable pharmaceutical agent 2 and the above-noted phosphor-containing drug activator 3 can be administered to the subject 4 by way of a sterile suspension of two or more of the above-noted phosphors. The initiation energy source may additionally be controlled by a computer system 5 that is capable of directing the delivery of the initiation energy (e.g., X-rays), In further embodiments, dose calculation and robotic manipulation devices (such as the CYBER-KNIFE robotic radiosurgery system, available from Accuray, or similar types of devices) may be included in the system to adjust the distance between the initiation energy source 1 and the subject 4 and/or to adjust the energy and/or dose (e.g., kVp or filtering) of the initiation energy source such that the x-rays incident on the target site are within a prescribed energy band. Further refinements in the x-ray energy and dose can be had by adjusting the distance to the subject 4 or the intervening materials between the target site and the initiation energy source 1. The initiation energy source 1 (i.e., an X-ray source) can provide images of the target area being treated.

In various embodiments, the initiation energy source 1 may be a linear accelerator equipped with at least kV image guided computer-control capability to deliver a precisely calibrated beam of radiation to a pre-selected coordinate. One example of such linear accelerators is the SMART-BEAM™ IMRT (intensity modulated radiation therapy) system (from Varian Medical Systems, Inc., Palo Alto, Calif.) or Varian OBI technology (OBI stands for "On-board Imaging", and is found on many commercial models of Varian machines). In other embodiments, the initiation energy source 1 may be commercially available components of X-ray machines or non-medical X-ray machines, X-ray machines that produce from 10 to 150 keV X-rays are readily available in the marketplace. For instance, the General Electric DEFINIUM series or the Siemens MULTIX series are two non-limiting examples of typical X-ray machines designed for the medical industry, while the EAGLE PACK series from Smith Detection is an example of a non-medical X-ray machine. Another suitable commercially available device is the SIEMENS DEFINITION FLASH, (a CT system), by Siemens Medical Solutions. As such, the invention is capable of performing its desired function when used in conjunction with commercial X-ray equipment.

In a particularly preferred embodiment, the initiation energy source 1 is a source of low energy x-rays, of 300 kVp or lower, e.g., at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp, In this embodiment, the initiation energy source provides low energy x-rays which are converted by the phosphor-containing drug activator 3 in situ to an energy capable of activating 8 MOP (or UVADEX).

In one embodiment of the invention, the phosphors in the phosphor-containing drug activator are first coated with a biocompatible Ethyl Cellulose coating, and then overcoated with a second coating of Diamond Like Carbon (DLC).

Ethyl Cellulose (EC) is widely used in biomedical applications today, including artificial kidney membranes, coating materials for drugs, blood coagulants, additives of pharmaceutical products, blood compatible materials. EC and its derivatives have been widely used in various, personal care, food, biomedical and drug related applications. EC is not a skin sensitizer, it is not an irritant to the skin, and it is not mutagenic. EC is generally regarded as safe (GRAS), and widely used for example in food applications such flavor encapsulation, inks for making fruits and vegetables, paper and paperboard in contact with aqueous and fatty foods.

EC is also widely used for controlled release of active ingredients. The enhanced lipophilic and hydrophobic properties make it a material of choice for water resistant applications. EC is soluble in various organic solvents and can form a film on surfaces and around particles (such as phosphors). In one embodiment of this invention, ethyl cellulose is used to encapsulate the phosphors particles of the phosphor-containing drug activator to ensure that an added degree of protection is in place on the surface of the phosphors. In one embodiment of this invention, EC polymers with high molecular weight for permanent encapsulation and long term biocompatibility are used to encapsulate the phosphors particles of the phosphor-containing drug activator. In a preferred embodiment, the EC polymer can be any commercially available pharmaceutical grade ethyl cellulose polymer having sufficient molecular weight to form a coating on the phosphor surface. Suitable EC polymers include, but are not limited to, the ETHOCEL brand of ethyl cellulose polymers available from Dow Chemical, preferably ETHOCEL FP grade products, most preferably ETHOCEL FP 100.

Diamond Like Carbon (DLC) films are in general dense, mechanically hard, smooth, impervious, abrasion resistant, chemically inert, and resistant to attack by both acids and bases they have a low coefficient of friction, low wear rate, are biocompatible and thromboresistant. Tissues adhere well to carbon coated implants and sustain a durable interface. In presence of blood, a protein layer is formed which prevents the formation of blood clots at the carbon surface. For medical prostheses that contact blood (heart valves, anathomic sheets, stents, blood vessels, etc.), DIX coatings have been used.

DLC has emerged over the past decade as a versatile and useful biomaterial. It is harder than most ceramics, bio-inert, and has a low friction coefficient. DLC is one of the best materials for implantable applications. Studies of the biocompatibility of DLC demonstrate that there is no cytotoxicity and cell growth is normal on a DLC-coated surface. (DLC coatings on stainless steel have performed very well in in vitro studies of hemocompatibility, Histopathological investigations have shown good biotolerance of implants coated with the DLC. Moreover, DLC as a coating is efficient protection against corrosion. These properties make the embodiment described here with a double coating (EC and DLC) particularly advantageous for the novel phosphor-containing drug activator of the invention.

Methods for coating the phosphors with EC or DLC are known to those of ordinary skill, and have been described, for example, in PCT/US2015/027058 filed Apr. 22, 2015, incorporated earlier by reference.

Manufacturing Process Steps

Figure 1B:
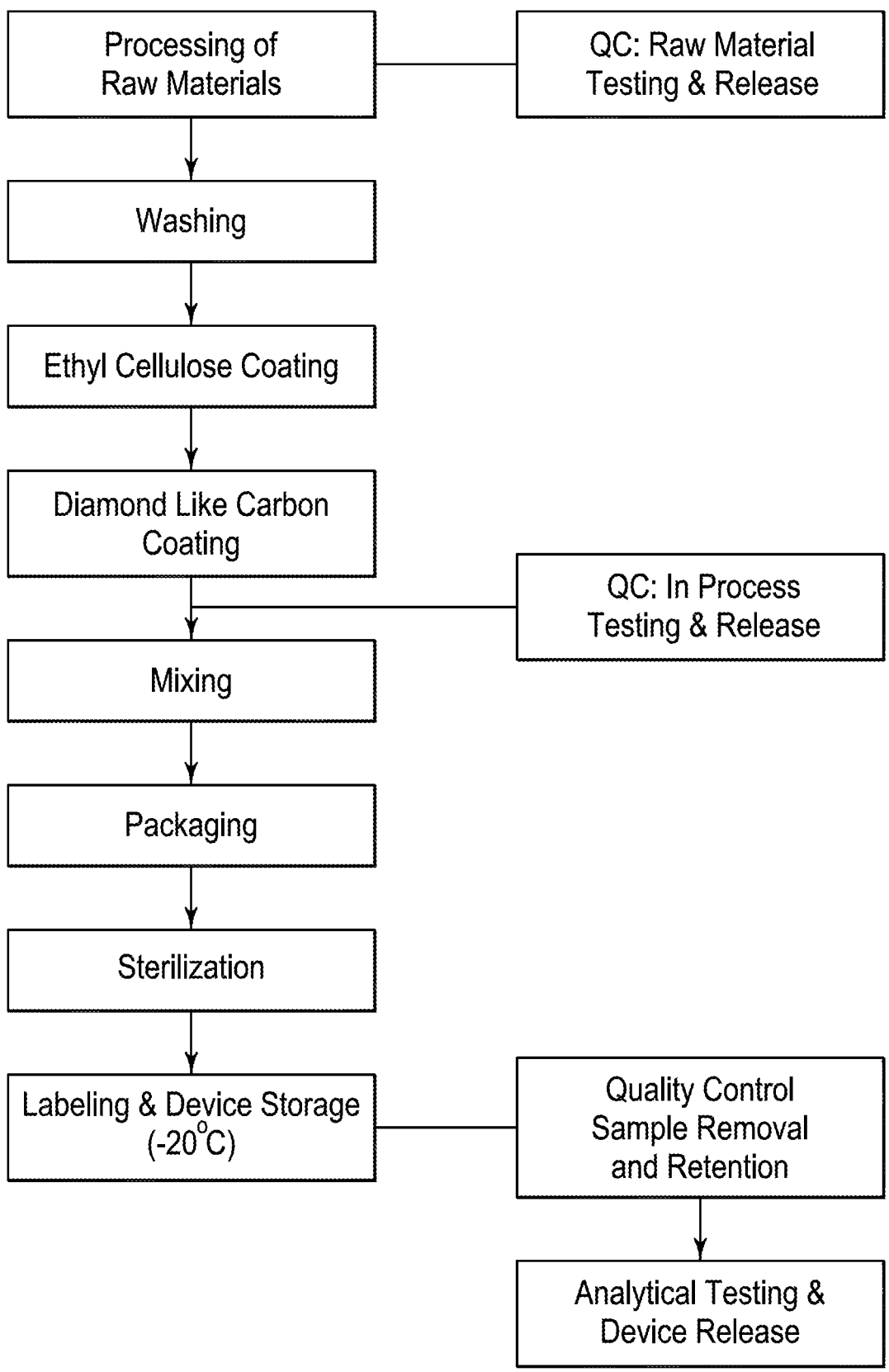
FIG. 1B is a flow diagram for one process of the invention for manufacturing the phosphor-containing device.

FIG. 1B is a flow diagram for one process of the invention for manufacturing the novel phosphor-containing drug activator using the raw materials noted in Table 1 below. (The present invention is not limited to the various steps described below in the illustrative manufacturing process. The steps merely provide specific ways that these steps can occur

TABLE 1

| Raw Materials | |
| --- | --- |
| Item Description/Name | Manufacturer |
| Phosphor GTP 4300 | Global Tungsten and Powders |
| Phosphor NP200 | Nichia |
| Ethyl Cellulose | Dow Chemical Co |
| Acetone | Thermo Fisher |
| Diamond like carbon (DLC | Fraunhoffer |

As shown in FIG. 1B, manufacturing of the novel phosphor-containing drug activator of the invention starts with quality control of the raw materials. As part of quality control, in one embodiment of the invention, the raw materials utilized in the novel phosphor-containing drug activator are characterized with one or more of the following suite of tests:

X-Ray Diffraction (XRD) to confirm the crystallography type;

X-Ray Photoelectron Spectroscopy (XPS) for surface elemental analysis;

Inductively Coupled Plasma (ICP) for total elemental analysis;

Scanning Electron Microscopy (SEM) for particle size determination;

Cathodoluminescence for UV/VIS emissions

X-ray diffraction (XRD) is nondestructive technique for characterizing crystalline materials. It provides information on structures, phases, preferred crystal orientations (texture), and other structural parameters, such as average grain size, crystallinity, strain, and crystal defects. The x-ray diffraction pattern is a fingerprint of periodic atomic arrangements in a given material. A comparison of an observed diffraction pattern to a known reference material allows confirmation of the crystal lattice of the solid material. In one embodiment of the invention, x-ray diffraction peaks matching known references form one acceptance criterion of the invention for further processing. Preferably, the $Zn_2SiO_4:Mn^{2+}$ phosphor has cathodoluminescent emission peaks at least at 160 nm, 360 nm, and 525 nm, while preferably the $(3Ca_3(PO_4)_2.Ca(F, Cl)_2: Sb^{3+}, Mn^{2+})$ phosphor has a cathodoluminescent emission edge at least at 400 nm and a cathodoluminescent emission peak at least at 570 nm.

X-ray Photoelectron Spectroscopy (XPS Analysis), also known as Electron Spectroscopy for Chemical Analysis (ESCA), is used to determine quantitative atomic composition and chemistry. It is a surface analysis technique with a sampling volume that extends from the surface to a depth of approximately 50-70 Angstroms. XPS analysis can be utilized to characterize thin films by quantifying matrix-level elements as a function of depth. XPS is an elemental analysis technique that is unique in providing chemical state information of the detected elements, such as distinguishing between sulfate and sulfide forms of the element sulfur. The process works by irradiating a sample with monochromatic x-rays, resulting in the emission of photoelectrons whose energies are characteristic of the elements within the sampling volume. In one embodiment of the invention, XPS is another acceptance criterion of the invention for further processing in which both the position (energy) of the emitted photoelectrons and their relative intensity patterns should match the reference patterns on file for each inorganic phosphor being used (e.g. NP200 and GTP430).

In one embodiment of the invention, this analytical method is used to determine the surface elemental composition of the raw material(s) and subsequent changes in atomic % of carbon to confirm that both the EC and DLC coating processes are within acceptable tolerances (e.g. up to a 25-75% increase in C content for the final EC/DLC autoclave product). As an acceptance criterion of the invention, emission peaks from Zn, Si, Ca, P, O, F, Cl, Sb, Mn and C should be present and no other elements (such as contaminants) would be present.

Inductively Coupled Plasma (ICP) analytical techniques can quantitatively measure the elemental content of a material from the ppt to the wt % range. In this technique, solid samples are dissolved or digested in a liquid, usually an acidic aqueous solution. The sample solution is then sprayed into the core of an inductively coupled argon plasma, which can reach temperatures of approximately 8000° C. At such temperature, analyte species are atomized, ionized and thermally excited. The analyte species is then detected and quantified with a mass spectrometer (MS). In one embodiment of the invention, XPS is another acceptance criterion of the invention in which both the mass number and intensity (relative quantity) should match reference patterns on file for each inorganic phosphor used (e.g. NP200 and GTP430).

Scanning Electron Microscopy (SEM) provides high-resolution and long-depth-of-field images of the sample surface and near-surface, SEM is one of the most widely used analytical tools due to the extremely detailed images it can provide. Coupled to an auxiliary Energy Dispersive X-ray Spectroscopy (EDS) detector, SEM also offers elemental identification for nearly the entire periodic table. In one embodiment of the invention, SEM/EDS screens raw and final materials for gross size and morphological particle analysis as well as a confirmation of elemental surface analysis of both our raw and processed materials. In one embodiment of the invention, SEM and/or EDS is another acceptance criterion of the invention in which the range of crystal sizes and/or elemental constituency is confirmed.

Cathodoluminescence is a technique that detects light emissions based on the specific chemistry of a crystalline lattice structure, Cathodoluminescence accelerates and collimates an electron beam toward a material (e.g., a phosphorous material). When the incident beam impacts the material, it causes the creation of secondary electrons and hole formation, the recombination of which leads to the emission of photons which are detected by a photospectrometer placed in close proximity to the material.

Figure 2:
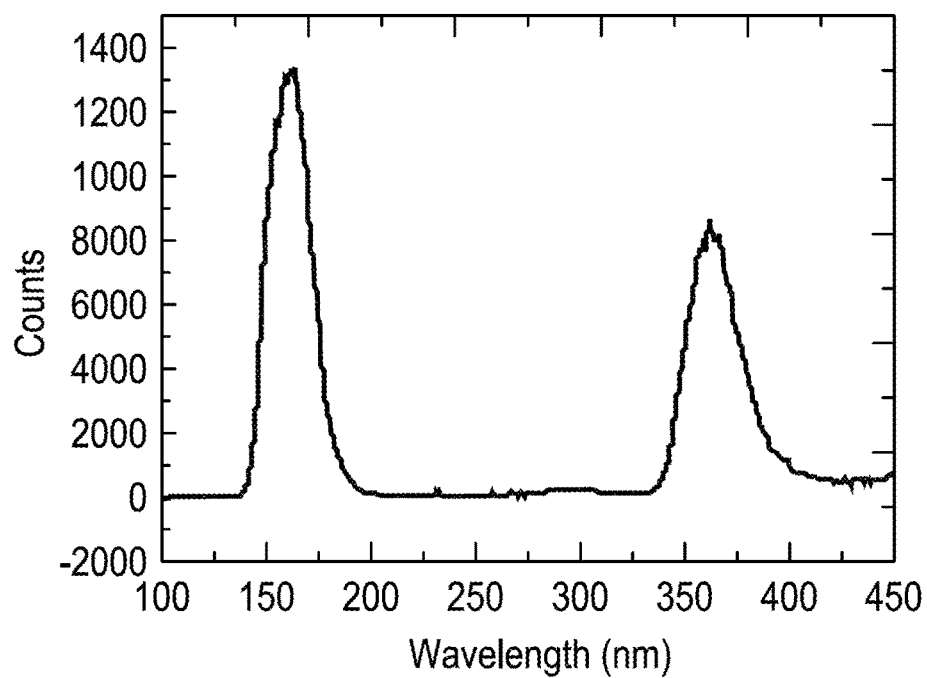
FIG. 2 is a depiction of cathodoluminescence data for $Zn_2SiO_4:Mn^{2+}$ measured between 100-400 nm.
Figure 3:
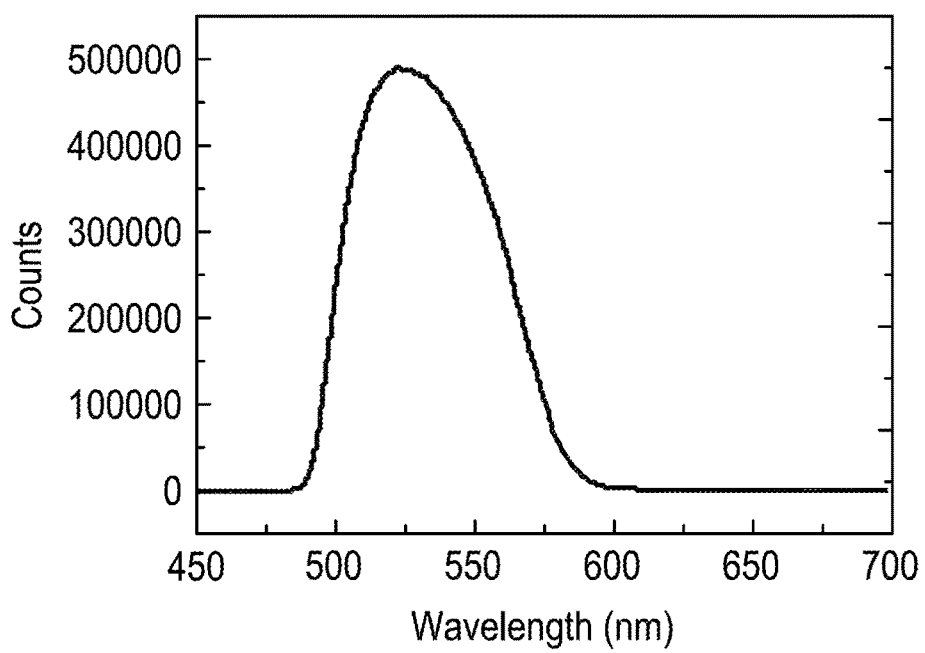
FIG. 3 is a depiction of cathodoluminescence data for $Zn_2SiO_4:Mn^{2+}$ measured between 450-700 nm.
Figure 4:
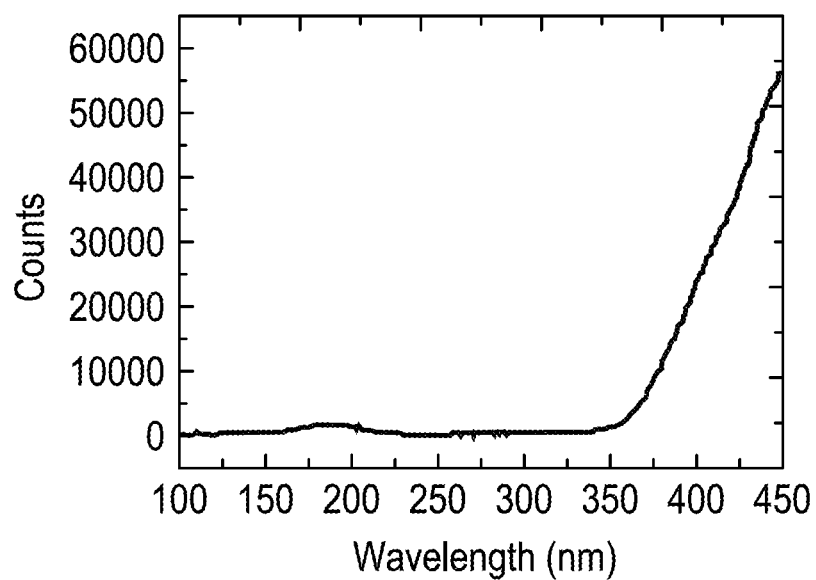
FIG. 4 is a depiction of cathodoluminescence data for $(3Ca_3(PO_4)_2.Ca(F, Cl)_2: Sb^{3+}, Mn^{2+})$ measured between 100-400 nm.
Figure 5:
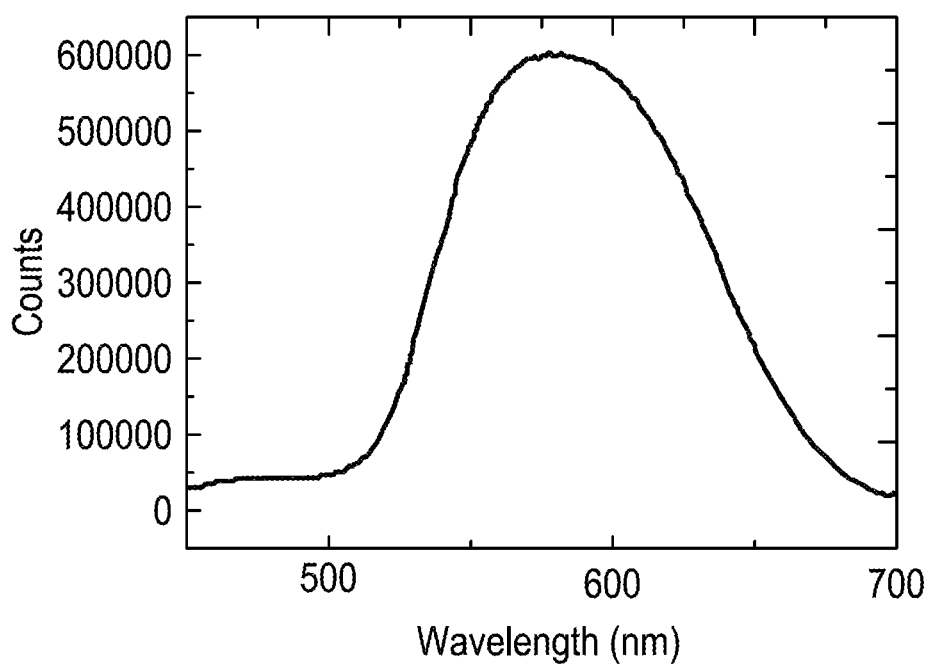
FIG. 5 is a depiction of cathodoluminescence data for $(3Ca_3(PO_4)_2.Ca(F, Cl)_2: Sb^{3+}, Mn^{2+}$ measured between 450-700 nm.

In one embodiment of the invention, a representative phosphor contained in the novel phosphor-containing drug activator would be tested by placing 10 mg inside a high vacuum chamber. The electron beam would be accelerated using a bias voltage of 1000V to 1500V. Obtaining at least 5000 counts (au) ensures that the material is emitting properly, and forms another acceptance criterion of the invention. Reference cathodoluminescence data for raw material phosphors are illustrated in FIGS. 2-5. FIG. 2 is a depiction of cathodoluminescence data for $Zn_2SiO_4:Mn^{2+}$ measured between 100-400 nm. FIG. 3 is a depiction of cathodoluminescence data for $Zn_2SiO_4:Mn^{2+}$ measured between 450-700 nm. FIG. 4 is a depiction of cathodoluminescence data for $(3Ca_3(PO_4)_2.Ca(F, Cl)_2: Sb^{3+}, Mn^{2+})$ measured between 100-400 nm. FIG. 5 is a depiction of cathodoluminescence data for $(3Ca_3(PO_4)_2.Ca(F, Cl)_2: Sb^{3+}, Mn^{2+})$ measured between 450-700 nm. In one embodiment of the invention, the cathodoluminescence emission wavelength of UV and visible light emitted. form an acceptance criterion of the invention.

The above described analytical testing is performed on purchased phosphors before these materials are accepted for use in manufacturing of the novel phosphor-containing drug activator. The test methods for the acceptance of the various raw materials in a preferred embodiment are specified below in Table 3.

TABLE 3

Acceptance Criteria for Raw Materials

| Parameter | Method |
| --- | --- |
| Phosphor crystalline phase | XRD |
| Surface elemental composition | XPS |
| Core elemental composition | ICP |
| Emission | CL |
| Size distribution | SEM |

As further shown in FIG. 1B, manufacturing of the novel phosphor-containing drug activator starts processing of the qualified raw phosphor materials by washing of the phosphor materials. More specifically, in one example, the phosphor materials are individually weighed with one gram (1 g) of phosphor placed in 50 mL plastic test tubes. Six mL of acetone are added and vortexed to thoroughly mix with the phosphors. The phosphors are pelletized via a low speed centrifuge, after which the excess acetone is removed. This cycle is repeated an additional two times for each of the two phosphors.

Figure 6:
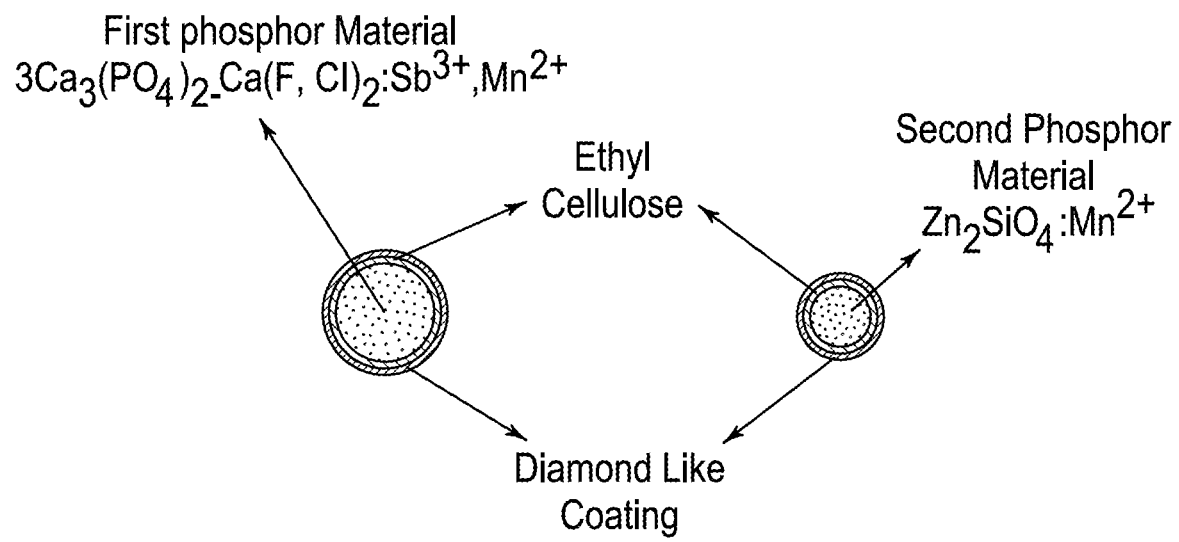
FIG. 6 is an illustration of a combination phosphor device having a dual coating.

As further shown in FIG. 1B, manufacturing of the novel phosphor-containing drug activator then coats each of the two phosphors first with ethyl cellulose, followed by a second coating consisting of diamond like carbon. Each of the phosphors constituting the phosphor containing device in one embodiment of the invention is independently doubly coated, before mixing the two phosphors together. FIG. 6 is an illustration of both phosphors (NP-200: $Zn_2SiO_4:Mn^{2+}$ and GTP-4300: $(3Ca_3(PO_4)_2.Ca(F, Cl)_2: Sb^{3+}, Mn^{2+}$ coated with a first coating (Ethyl-Cellulose) and a second coating (Diamond-Like-Carbon).

For the ethyl-cellulose coating, in one preferred embodiment of the invention, the phosphor particles are encapsulated based on the parameters provided in Table 4.

TABLE 4

Preferred thickness of the EC coating

Ethyl Cellulose Coating

| Target Thickness (nanometers) | 30 |
| --- | --- |
| Phosphor Density (g/cc) | 7.5 |

As further shown in FIG. 1B, manufacturing of the novel phosphor-containing drug activator in one embodiment of the invention then coats each of the two phosphors with a secondary coat of DLC by Physical Vapor Deposition to further encapsulate the phosphors and to further enhance their biocompatibility.

For the DLC film, a preferred thickness is 100 nm +/−3 nm, and a preferred Elastic Modulus is 45-55 Gpa, most preferably 50-53 Gpa.

The PVD coating machine is equipped with various process control sensors and interlocks to ensure reproducibility.

The contact angle of non-coated glass and non-coated silicon are 19 degrees and 65 degrees respectively. After the coating process, the contact angles are preferably 100° +/−10%. The contact angle (for a water droplet) of both substrates is targeted to be between 90 and 110°. The water droplet contact angle provides another acceptance criterion of the invention.

Specific release specifications for in-process testing are specified in the table below:

TABLE 7

Release Specifications for In-Process Test Material

| Parameter | Method |
| --- | --- |
| Coating thickness | Step Height |
| Size distribution | Scanning |
| Surface elemental composition | XPS |

As further shown in FIG. 1B, manufacturing of the novel phosphor-containing drug activator in one embodiment of the invention continues by mixing the two types of coated phosphors. The phosphor-containing drug activator as noted above is made of a combination of two phosphors. Specifically, NP-200 ($Zn_2SiO4:Mn^{2+}$) is mixed with GTP-4300 ($3Ca3(PO4)2.Ca.(F, Cl)2: Sb3+, Mn2+$) at a ratio NP-200:GTP-4300 of from 1:10 to 10:1, or from 1:5 to 5:1, or from 1:2 to 2:1, or about 1:2.

Figure 7:
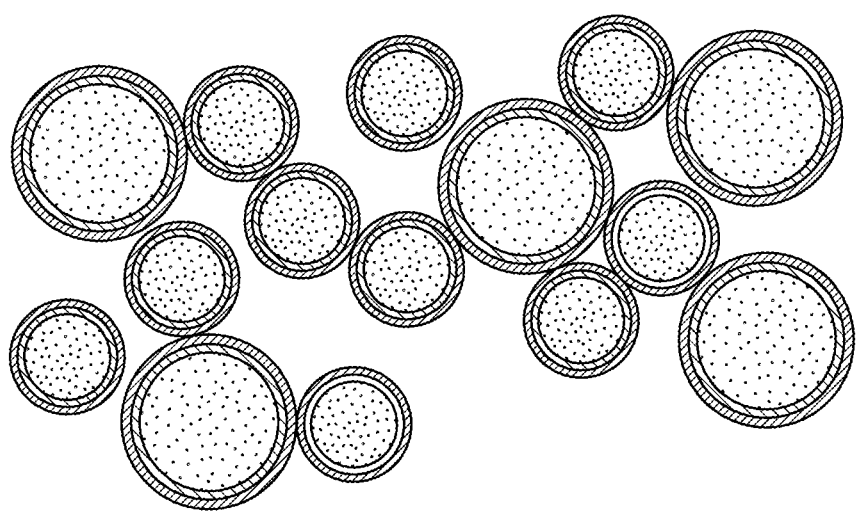
FIG. 7 is an illustration of a combination phosphor device having a 2:1 ratio with one part of $Zn_2SiO_4:Mn^{2+}$ for every two parts of $(3Ca_3(PO_4)_2.Ca(F, Cl)_2: Sb^{3+}$.

FIG. 7 is a representative illustration of the mixture of phosphors constituting the phosphor-containing device. (The efficacy of this mixture has been determined in vitro by assessing the cell kill brought about by the addition of the drug alone, mixture of phosphors alone, and then the mixture of drug and phosphors under X-Ray energy.)

As further shown in FIG. 1B, manufacturing of the novel phosphor-containing drug activator in one embodiment of the invention continues by packaging of the combination phosphor-containing device. Specifically, the phosphor-containing drug activator is aseptically pre-weighed and packaged in sterile, nonpyrogenic 10 mL borosilicate amber glass vials. These vials come equipped with a 20 mm crimp neck, fitted with a 20 mm butyl rubber stopper and finally crimp sealed with 20 mm flip-top aluminum seals. The final amount of device per sterile container is specified by a kit number.

In one embodiment of the invention, multiple treatment kits can be prepared to accommodate different tumor sizes, with each vial designed for example to deliver 0.6 mg of phosphors per cubic centimeter of tumor volume.

Specifics of the container closure system are listed below in , although other sterile enclosure systems or enclosure systems that can be sterilized are suitable for this invention.

TABLE 8A

Container Closure Components

| Item Description/Name | Manufacturer |
| --- | --- |
| 10 mL amber glass vials, 20 | Wheaton |
| 20 mm butyl rubber stopper | Wheaton |
| 20 mm aluminum flip cap | Wheaton |

All device vials are cleaned and depyrogenated by the manufacturer according to standardized procedures. After filling the vials with the phosphor-containing drug activator device, vials are stoppered with the butyl rubber septum top. The stoppered vials are then crimp sealed employing a flip-off seal and sent for sterilization.

Figure 8:
FIG. 8 is a photographic depiction of a packaged device kit according to one embodiment of the invention.

As further shown in FIG. 1B, manufacturing of the novel phosphor-containing drug activator in one embodiment of the invention continues by sterilizing the vials. Specifically, crimp sealed vials are autoclaved for 30 minutes (thy-cycle, 250° F. at 14 PSI) and immediately removed from the autoclave. Sterile vials are visually inspected and affixed with an adhesive label (heat resistant, permanent ink) that specifies contents, packaging lot number and date of preparation. Labeled vials are then placed in labeled boxes fitted with individual vial partitions. Sealed cases of devices are labeled with a lot number and shipped. FIG. 8 is a photographic depiction of on example of final, packaged device kit according to one embodiment of the invention in which the device kit includes the novel phosphor-containing devices described above.

As further shown in FIG. 1B, manufacturing of the novel phosphor-containing drug activator in one embodiment of the invention continues by device storage. The sterile materials of the novel phosphor-containing drug activator should be kept at room temperature (20-30° C.) in a humidity controlled environment. Dark storage is preferred but not required.

As further shown in FIG. 1B, manufacturing of the novel phosphor-containing drug activator continues to steps ensuring quality control and retention of the characteristics noted above corroborated by analytical testing before product release. Table 8B below shows a listing of acceptance criteria for the novel phosphor-containing drug activator prior to the phosphor-containing drug activators being mixed with a pharmaceutically acceptable carrier and/or UVADEX.

TABLE 8B

Acceptance Criteria for the Phosphor-Containing Devices

| Parameter | Method |
|---|---|
| Size | SEM |
| Emissions | Cathodoluminescence |
| Coating | XPS |
| Biocompatibility | Chemical extraction and toxicological risk assessment per ISO 10993-17<br>Cytotoxicity: 10993-5<br>Sensitization: 10993-10<br>Irritation: 10993-10<br>Systemic toxicity: 10993-11<br>Implantation: 10993-6 |
| Pyrogenicity | USP 34 <151> |
| Sterility | USP <71> |
| Bacterial Endotoxin | USP <85> |

United States Pharmacopeia (USP) is a compendium of quality control tests for drugs and excipients to be introduced into a medicinal formulation. It is published every year by the United States Pharmacopoeial Convention.

In one embodiment of the invention, preparation of the vials will be performed under USP 797 guidelines for compounding sterile preparations. Specifically, using a sterile syringe and 18-20 Ga needle, the novel phosphor-containing drug activator will be hydrated with a specified volume of sterile UVADEX (psoralen). The contents of the vial will be vortexed for a minimum of 3 minutes to ensure proper phosphor dispersion, after which the contents of the vial will be transferred into a standard syringe. The treatment administration syringe will be labeled, at a minimum, with the following information: Subject name, subject number, device name, e1RB #, dose due date and time, pharmacist initials. Immediately following preparation, the device preparation will be delivered to the treatment area for administration to the subject.

In one embodiment of the invention, multiple treatment kits can be prepared to accommodate different tumor sizes, with each vial designed to deliver a consistent mass of phosphors per cubic centimeter of tumor volume. Specifically, five (5) treatment kits can be prepared in accordance with Table 9 below.

TABLE 9

Kit Packaging- Device Weight Per Kit

| Treatment Group | Tumor Volume (cubic centimeters) | UVADEX Hydration Volume (mL) | Final (mg/mL) | Total Phosphor (mg/ sterile vial) |
|---|---|---|---|---|
| TG-1 | <15 | 0.75 | 10 | 7.5 |
| TG-2 | 15.1 - | 1.5 | 10 | 15.0 |
| TG-3 | 30.0 - | 3 | 10 | 30.1 |
| TG-4 | 50.0 - | 4 | 10 | 40.1 |
| TG-5 | >75 | 5 | 10 | 50.2 |

Device Administration and Activation

Administration in one embodiment of the invention is preferably by intratwnoral injection immediately prior to irradiation, at a total volume 0.033-0.067 mL per $cm^3$ tumor, including 0.33 to 0.667 mg phosphor per $cm^3$ tumor. In one embodiment of the invention, the phosphor-containing drug activator including the UVADEX will be administered in multiple injections across the tumor.

In one embodiment of the invention, immediately after injection, the phosphor-containing drug activator will be activated with a low dose X-ray from an on-board imaging (OBI) system of the treatment linear accelerator. The prescribed dose is 0.6 to 1.0 Gy per fraction.

In one embodiment of the invention, the radiation delivery is set such that 1 Gy of radiation is delivered per fraction using 80 kVp X-rays from the OBI on the linac CT. In one embodiment of the invention, immediately following intratumoral injection, the region of interest will be exposed to a low dose kilovoltage radiation, by acquiring a cone beam CT (CBCT). At least one rotational kilovoltage CBCT can be utilized such that images can be stored for future evaluation. Subsequent CBCT s can be shared if there has been a significant reduction in tumor volume such that RT re-planning is necessary to avoid overdosing normal tissues adjacent to the tumor.

In one embodiment of the invention, activation of the phosphor-containing drug activator can be performed using 1.0 Gy of 80-100 kVp of x-ray energy delivered from a CT device. Accordingly, the in vivo phosphor-containing drug activator in one embodiment absorbs low energy x-rays from commercially available, FDA-cleared CT scanners and re-emits that energy in wavelengths that overlap with the absorption spectra of UVADEX, an FDA approved drug that promotes apoptosis of tumors cells by for example forming photoadducts with DNA, resulting in inhibition of DNA synthesis and cell division.

Murine Studies

A trial has been conducted for an evaluation of treatment administered to syngeneic 4T1-HER2 tumors grown on BALB/c mice. There were 4 arms of this trial: (1) saline only (control), (2) phosphors alone with x-ray, (3) psoralen (AMT) alone with x-ray, and (4) full treatment including both phosphor and psoralen and x-ray irradiation. Treatments were given in 3 fractions per week, to a total of 6 fractions. In arms 2-3 a consistent x-ray irradiation technique was used (0.36 Gy delivered at 75 kVp by 30 mA in 3 minutes) with 100 μg of phosphor, and 5 μM psoralen (AMT). 0.5 Million 4T1-HER2 cells were injected subcutaneously to the right thigh of each mouse. There were 6-8 mice per arm, and the study was repeated a second time, yielding effective sample sizes of 12-16.

Figure 9A:
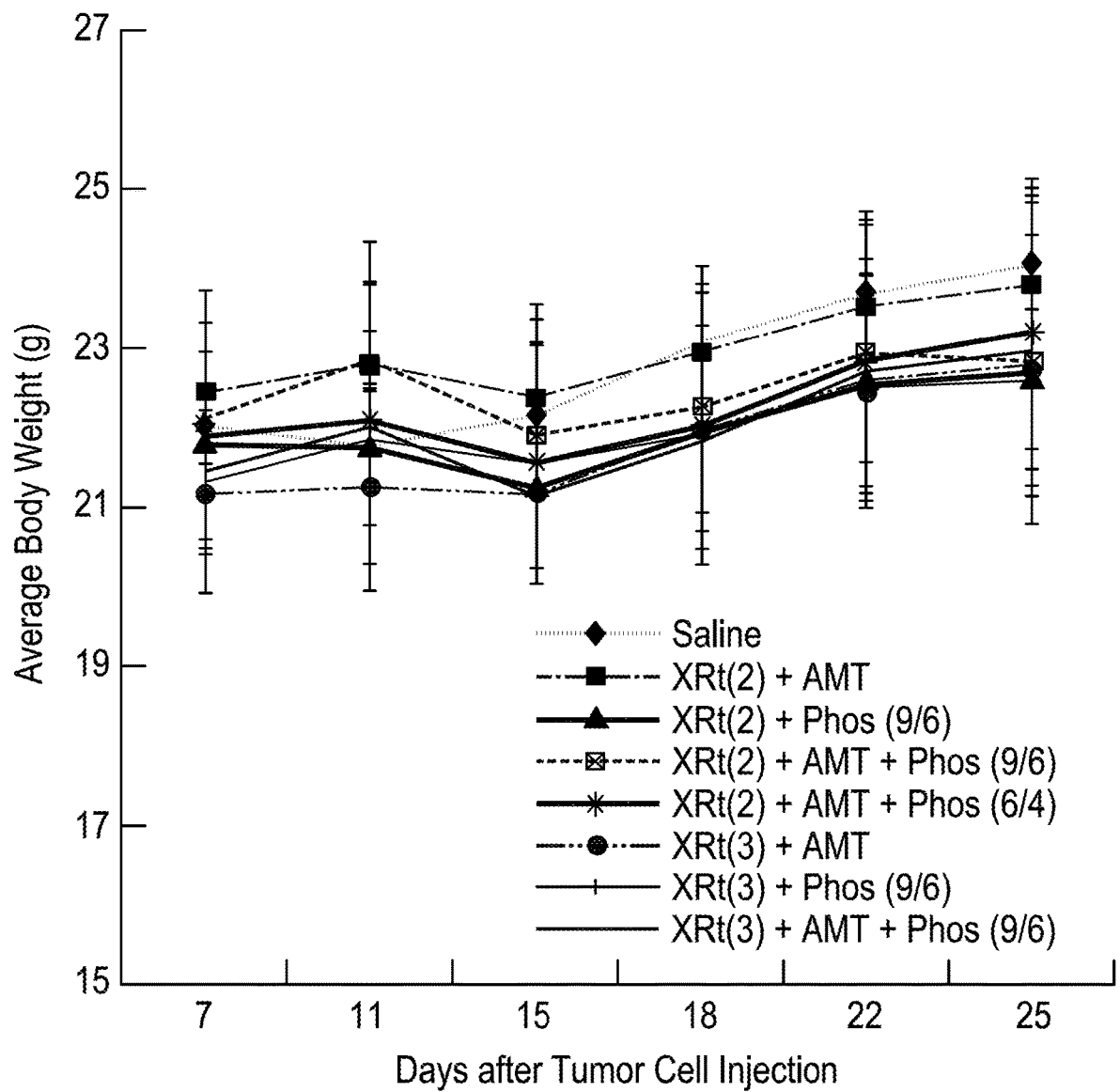
FIGS. 9A, 9B, 9C, 9D, and 9E show graphs showing tumor volume as a function of days after treatment for an in-vivo treatment of BALBC mice with syngeneic 4TI-HER2 tumors, as well as photographs of tumors being treated during the course of treatment.
Figure 9B:
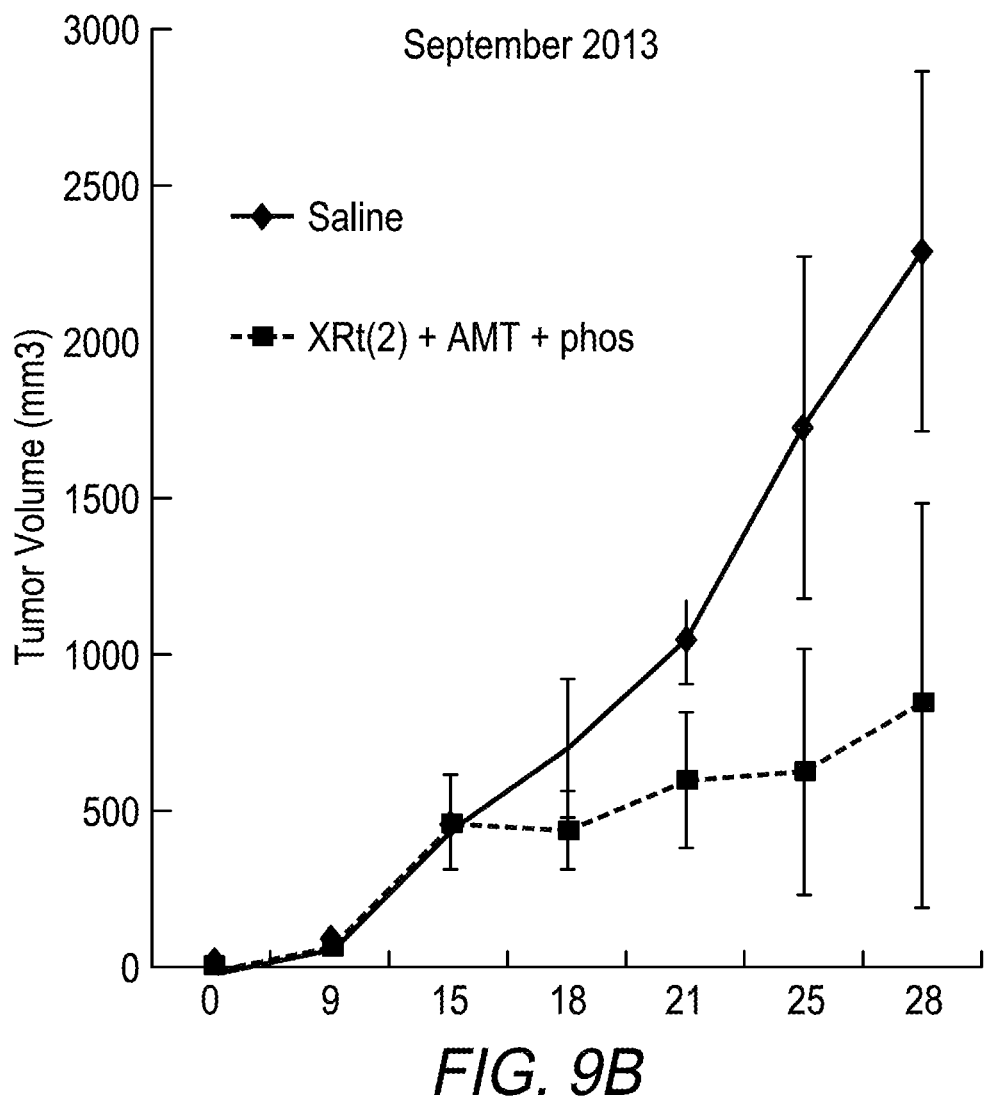
Figure 9C:
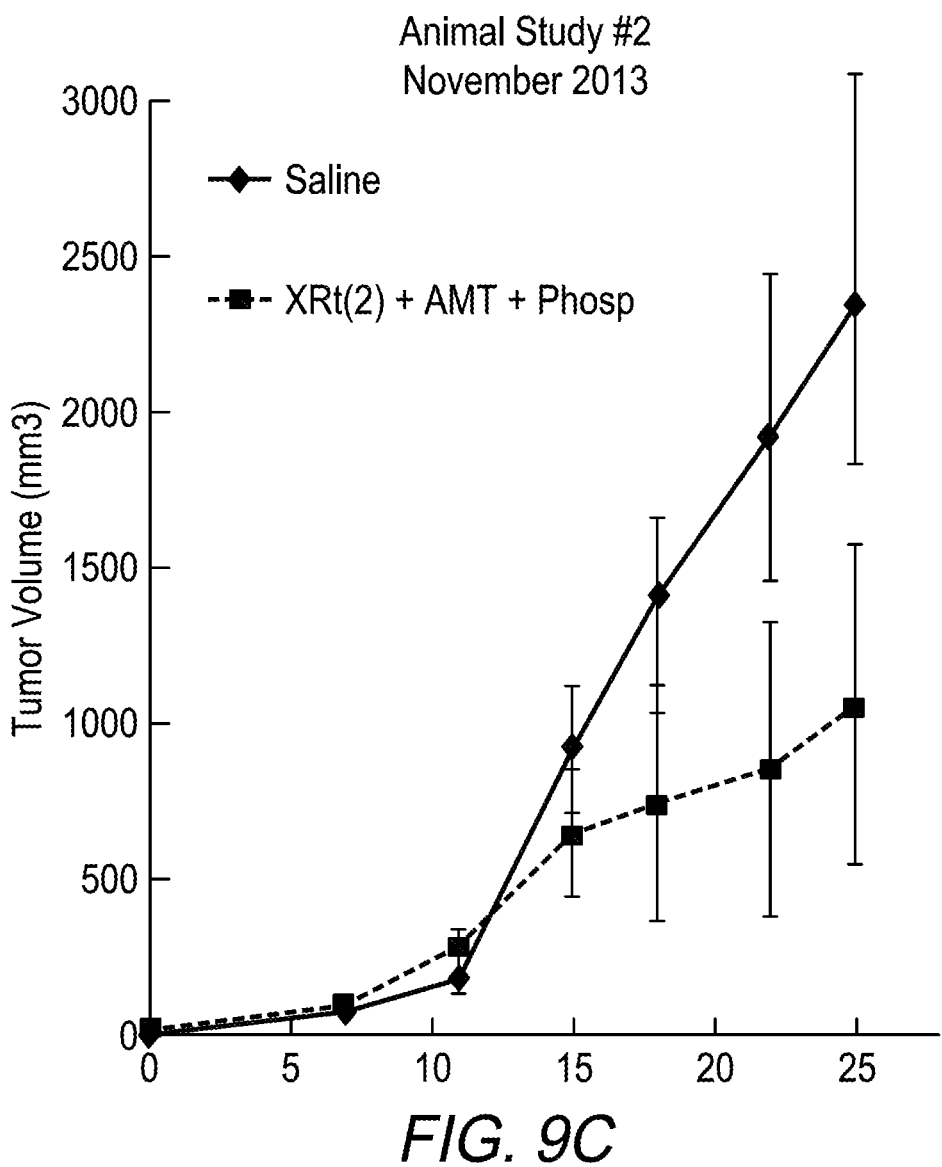

The results from the in-vivo treatment of BALBC mice with syngeneic 4T1-HER2 tumors are shown in FIGS. 9A-9E, The toxicity of the treatment was evaluated by the monitoring of the average body weight for different arms of the treatment, as shown in FIG. 9A. There was no significant loss in body weight for any of the arms. Meanwhile, the data in FIGS. 9B and 9C show the suppression of tumor growth as compared to a saline injection.

Figure 9D:
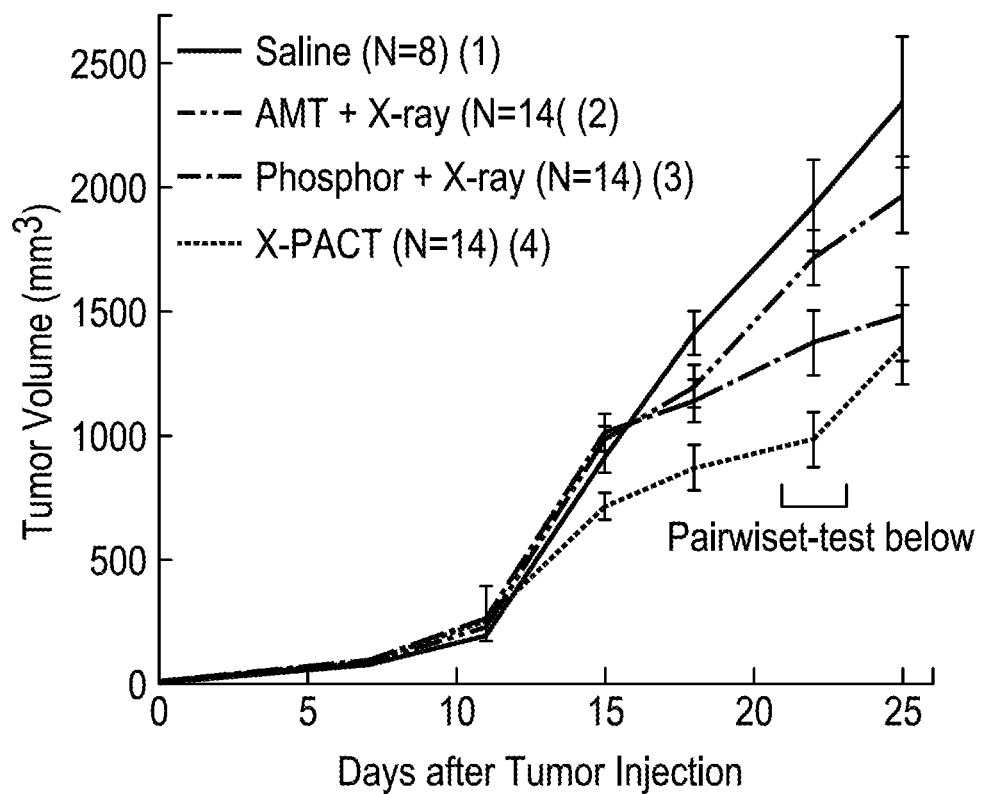

In FIG. 9D, the overall saline controls are indicated by line (1). The two other component control arms correspond to 5 μM psoralen (AMT) only, and 100 μg of phosphor only and are shown as lines (2) and (3). respectively. A consistent x-ray irradiation technique was used for all arms (except saline control) which was 0.36 Gy delivered at 75 kVp by 30 mA in 3 minutes. (The full treatment, consisting of the device, drug and X-ray, is depicted as x-ray psoralen activated cancer therapy X-PACT, indicated by line (4).)

Figure 9E:
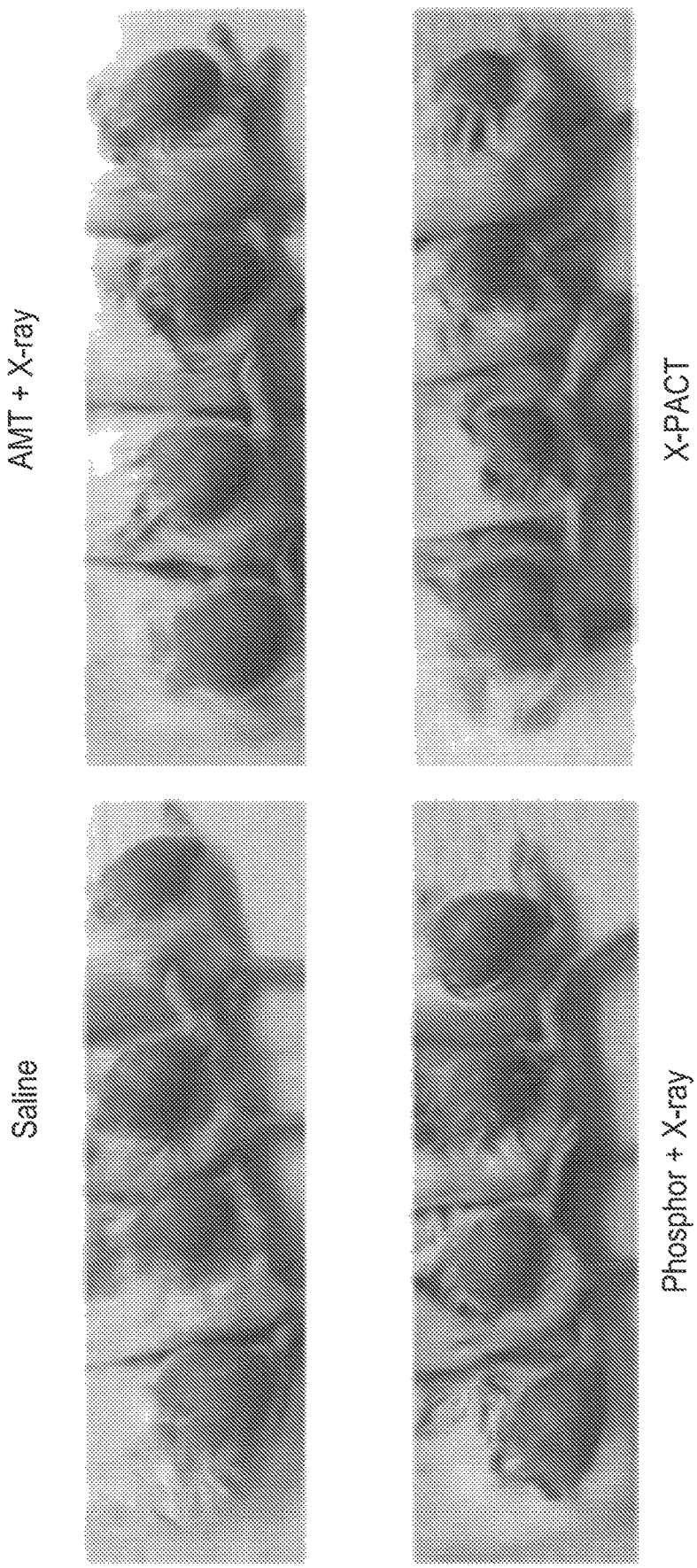

The first treatment was delivered to the syngeneic 4T1-HER2 tumors, on day 10 after implantation of the 4T1-HER2 tumors. Over the next two weeks a growth delay was observed in the treatment arm, compared to controls. Encouragingly, by day 25, there was a 42% reduction in tumor volume (p=0.0002). FIG. 9E shows a photographic depiction showing a comparison of the tumors from different mice at different times after exposure of the mice to different arms of the treatment.

In Vitro Studies

In-vitro studies were conducted on a 4T1 (murine breast cancer) cells incubated in appropriate growing media and buffers before being trypsinized and plated evenly onto twelve (12) well plates for 24 hours. About 20 minutes prior to irradiation, the wells of each plate were exposed to the following combinations of additives: (1) Control–cells only with no additives, (2) UVADEX only, (3) phosphors only, (4) UVADEX+phosphors. Each plate had twelve (12) wells with three wells for each of the four treatment arms. The plates were then irradiated with x-rays by placing the plate at a known distance from the x-ray source (e.g., 50 cm). After irradiation, the cells were incubated on the plate for 48 hours prior to performing flow cytometry. Guava AnnexinV flow cell cytometry was used to quantify cytotoxicity. The live cells were quantified, and the numbers of cells undergoing early or late apoptosis were measured. The treatment was then contrasted using a figure of merit referred to as the fractional cell kill (or the % of cells that were no longer viable). Table 10 shows this figure of merit for different ratios. The final amount of phosphor used in each case was kept at 50 micro-grams. The mixture of phosphors consisting of a 1:2 ratio by weight leads to better fractional cell kill. However, the results showed the efficacy of the present invention over a wide range of ratios and when using only one or the other of the phosphors noted above.

TABLE 10

Fractional Cell Kill with Different Phosphor Ratios

| NP-200 | GTP-4300 | NP-200/GTP-4300 | Fractional Kill |
|---|---|---|---|
| 100% | 0% | 1:0 | 4.70% |
| 33% | 67% | 1:2 | 25.10% |
| 0% | 100% | 0:1 | 13.30% |

X-Ray Activation of the Phosphor-Containing Drug Activator

In one embodiment of the invention, the initiation energy that is used to activate the phosphor device is delivered through a series of x-ray pulses consisting of a programmable kV, a set distance from the source, an amperage, and a time. The preferred setting for x-ray pulsing that activates UVADEX in the presence of phosphors consists of a distance of 50 cm, 80 kV, 200 mA and 800 ms. Each of these pulses is repeated a number of times to achieve the desired dose. To obtain a dose of 1 Gy, twenty one (21) such pulses are needed. The time between these programmable pulses is optimized at 10 sec. It was found that the process is stable and that small variations in any of the settings do not lead to drastic changes in the results.

Figure 10:
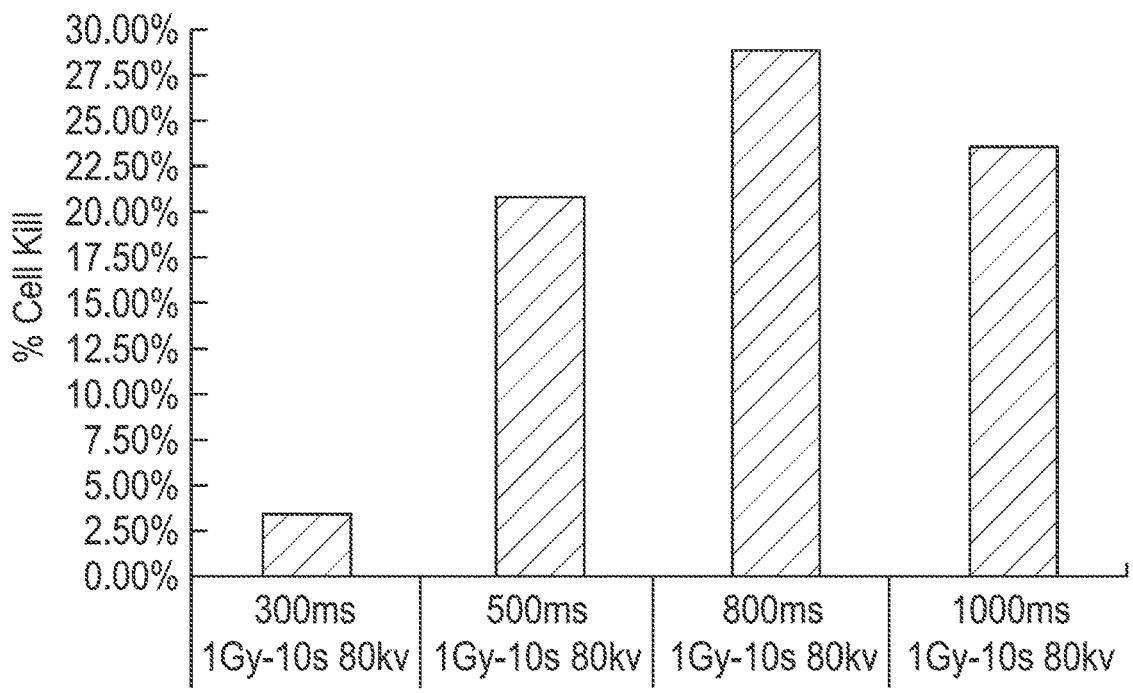
FIG. 10 is a plot summarizing the fractional cell kills as a function of kVp for a fixed amperage of 200 mA.

FIG. 10 is a summary of the fractional cell kill. FIG. 10 illustrates that the best results were obtained at 80 kV, 800 ms for a fixed amperage of 200 mA.

Figure 11:
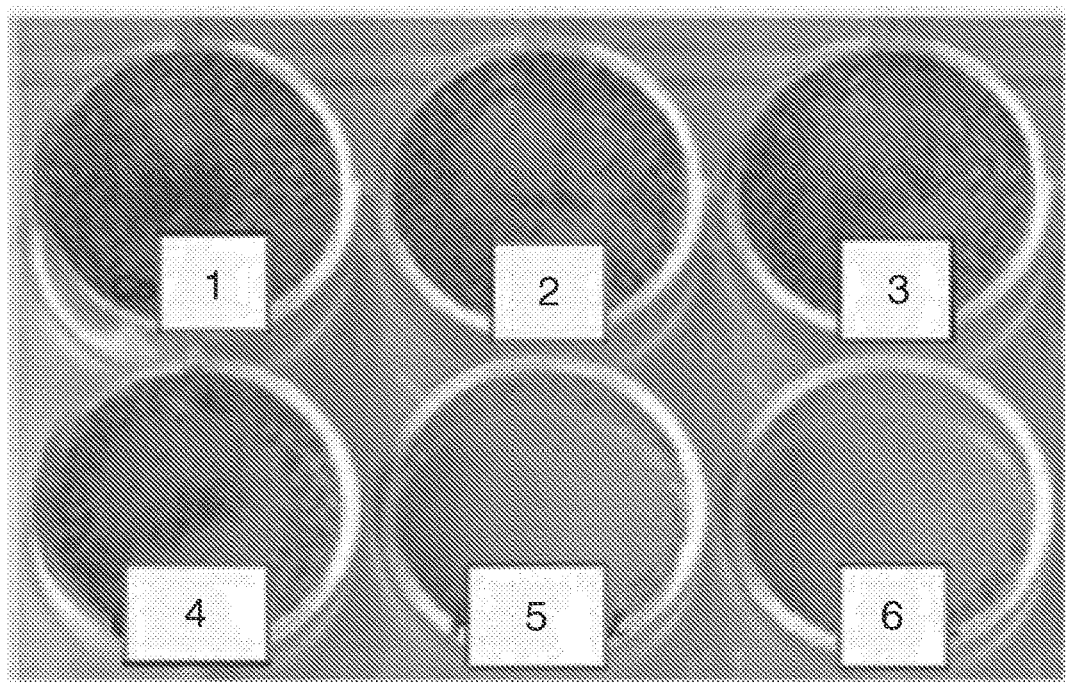
FIG. 11 is a photographic depiction showing of methylene blue staining for cell viability post treatment with x-rays, phosphors, and UVADEX.

Methylene blue staining of viable 4T1-HER2 cells confirms that the device works well according to the target parameters identified above. A plate having six (6) wells is subjected to treatment. FIG. 11 is a photographic depiction showing of Methylene Blue stain for cell viability post treatment with X-ray, phosphors and UVADEX. One well (#1) is the control. One well (#2) has phosphor coated with EC and DLC (H100). One well (#3) has phosphor coated with EC (but no DLC). One well (#4) has drug UVADEX but no phosphors. One well (#5) has drug UVADEX and phosphors coated with EC and DLC. One well (#6) has drug UVADEX. and phosphors coated with EC and no DLC.

All wells were exposed to the optimized x-ray initiation energy noted above. The combinatory effect of drug plus phosphors is evident and leads to cell death more effectively than the other conditions. The EC coated phosphors and the EC and DLC coated phosphors both work effectively. One added benefit to a dual coating is redundancy in safety of the treatment.

Figure 12:
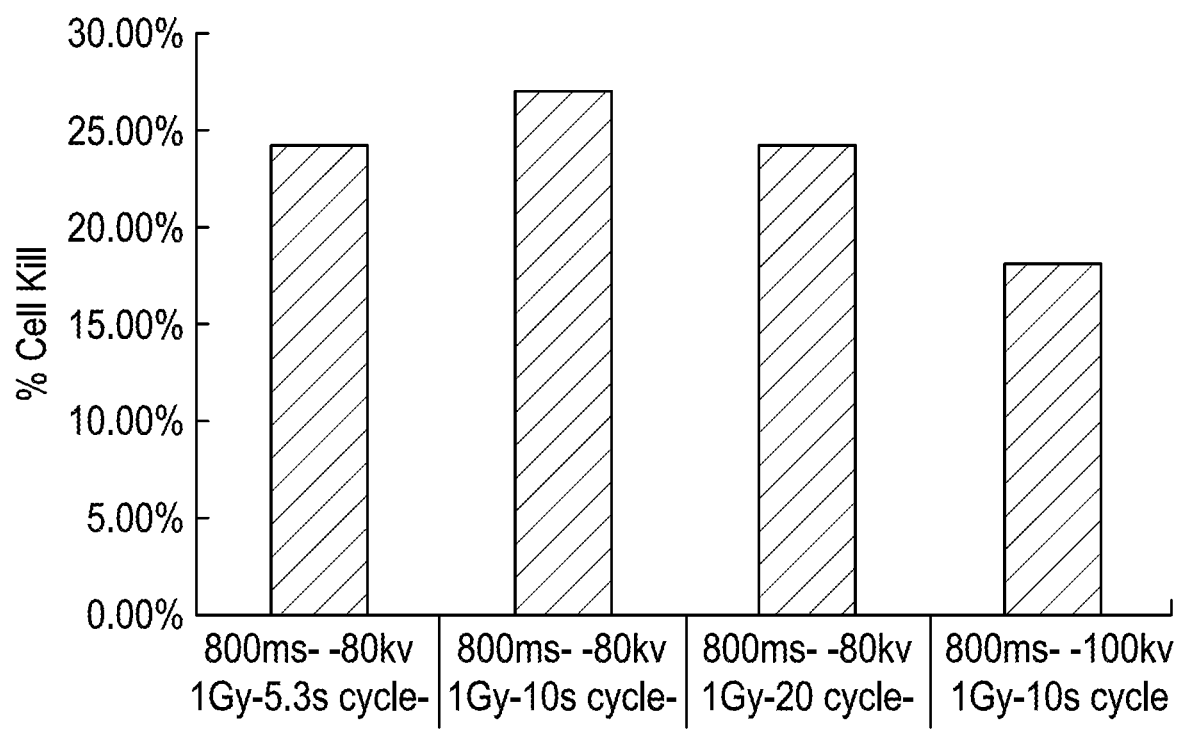
FIG. 12 is a plot summarizing the fractional cell kills under different x-ray exposure cycles.

The elapsed time between the various x-ray pulses was considered as a variable. The x-ray pulses were delivered using 5.3 seconds cycles between pulses. These tests were compared to cycles of 10 sec and 20 seconds between cycles. FIG. 12 is a plot showing the optimum cycle time between pulses. The cycle time that best optimizes the fractional cell kill is 10 sec between pulses. So, in effect, a dose of 1 Gy is delivered using twenty one (21) X-Ray pulses spaced apart by 10 seconds; and, each x-ray pulse consists of the following settings: 80 kV, 800 ms, 200 mA. These were the settings used in the follow on canine in-vivo studies.

Quantification of Cytotoxicity and Apoptosis

Guava Annexin V flow cell cytometry was used to quantify cytotoxicity in 3 murine tumor cell lines (mammary -4T1; 4T1-HER2, 4T1 stably transfected with the human HER2 oncogene; glioma-CT2A; sarcoma KP-B). The mouse breast cancer cell line 4T1 was purchased from ATCC. 4T1-HER2 was provided by Dr. Michael Kershaw (Cancer Immunology Program, Peter MacCallum Cancer Centre, Victoria, Australia) and maintained in DMEM with penicillin/streptomycin and 10% FBS The Sarcoma KP-B cell lines were derived from primary tumors LSL-Kral; p53 Flox/Flox mice (45).

Tumors between 250 and 300 cm$^3$ were digested using a mixture of collagenase/dispase/trypsin for 1 hour, passed through a 70-micron filter, and cultured 5 to 8 passages before being used for experiments. Cells were cultured in DMEM medium supplemented with 10% FBS and incubated at 37° C. with 5% $CO_2$ in a humidified cell-culture incubator.

In-vitro studies were conducted on plated cells following standard procedures. Cells were maintained in RPMI-1640 supplemented with 10% fetal bovine serum and L-glutamine from GIBCO (Grand Island, N.Y.) growing in a humidified atmosphere of 5% $CO_2$. After incubation, cells were trypsinized and plated evenly onto twelve 12-well plates for 24 hours. About 20 minutes prior to irradiation, the 12 wells of each plate were exposed to the following combinations of additives: (1) control–cells only with no additives, (2) UVADEX only, (3) phosphors only, (4) UVADEX+phosphors. Each plate had 12 wells with three wells for each of the four treatment arms. The plates were then irradiated with x-rays by placing the plate at a known distance from the x-ray source (50 cm). After irradiation, the cells were incubated on the plate for 48 hours prior to performing flow cytometry. For compatibility with 96-well Guava Nexin® assay, the remaining cells were again trypsinized. (after the 48 hour incubation) and plated onto the 96-well plate, A range of x-ray activation protocols were investigated to determine the cytotoxic efficacy in relation to x-ray energy (kVp), total dose, and dose-rate. kV beam energies ranging between 80-100 kVp were investigated. kV beams were obtained from various x-ray generating equipment, including orthovoltage units, standard diagnostic radiographic, fluoroscopic, and cone-beam computed tomography (CBCT) systems. The primary kV x-ray source utilized in the in vitro studies (for all data presented, unless stated otherwise in the figure caption) was a Varian on-board-imaging x-ray source commonly found on Varian medical linear accelerators. The x-ray dose delivered for the in-vitro irradiations studied here ranged from 0.2-2 Gy, with main emphasis on lower doses of 0.5-1 Gy.

For x-ray irradiation, the well plates were positioned at a set distance (typically 50 cm) from the x-ray source on a solid water phantom and the position of the well plates within the x-ray beam was verified by low dose kV imaging. Irradiations were typically delivered in a "radiograph" mode; where multiple pulses of a set mA (typically 200) and ms (typically 800) and pulses were delivered every 5-15 seconds. In experiments investigating dose-rate effects, the radiation was also delivered in a "pulsed fluoroscopy mode" (10 Hz) at the maximum mA setting. The most common kVp settings were 80 and 100 kVp with no added filtration in the beam (Half Value Layer=3.0 and 3.7 mm Al, respectively).

Two primary flow cytometry analyses were used, both determined at 48 hours after treatment. Cells plated in 12-well plates, where individual wells in each plate received different experimental conditions (e.g., psoralen concentration), but the same x-ray dose all wells in a given plate receive the same x-ray dose). The first analysis evaluated was metabolic cell viability (herein referred to as cell viability) calculated from the number of whole cells per well as determined using forward scattering (ESC). For each well, cell viability was normalized to that in a control well without psoralen or phosphors but which did receive radiation. (All wells on a given plate receive the same dose.) The second assay is Annexin V positivity, which is the fraction of viable cells that are Annexin V+ by flow cell cytometry. The Annexin V (+) signal was corrected by subtracting the control signal from the no-psoralen/phosphor well on the same plate.

Other assays were used to provide independent complimentary information on cell viability, e.g. Methylene blue staining and ATP-induced Luminescence imaging (Cell-Titer-Glo® Luminescence Cell Viability Assay). The luminescence imaging permitted investigation of the cytotoxicity of psoralen activated directly with a UV lamp, and in the absence of phosphors and x-ray radiation.

Several statistical analyses were completed, including unequal variance two-sample t-tests, Analysis of Variance (ANOVA), and multi-variable regression. The unequal variance two-sample t-test tests the null hypothesis that the means of observations (e.g. viable cells, Annexin signal) in two different populations are equal. The p-value gives the probability that the observed difference occurred by chance. Multi-variable regression was used to test the null hypothesis that psoralen and phosphor had no effect on Annexin V (+) signal and to test if there is a first-order interaction between the two therapeutic elements. Non-parametric statistical analysis were also performed for each test, and showed consistent results.

Results of statistical analyses are classified in four categories: weakly significant, moderately significant, significant, and very significant. A single asterisk indicates weakly significant statistics (*), where the p-value is in the range $0.01<p<0.05$. Double asterisks indicate moderately significant statistics (), where $0,001<p<0.01$. Triple asterisks indicate significant statistics (*), where $0,0001<p<0.001$. Quadruple asterisks indicate very significant statistics (****), where $p<0.0001$. This convention will be used throughout the Results and Discussion section.

Figure 13A:
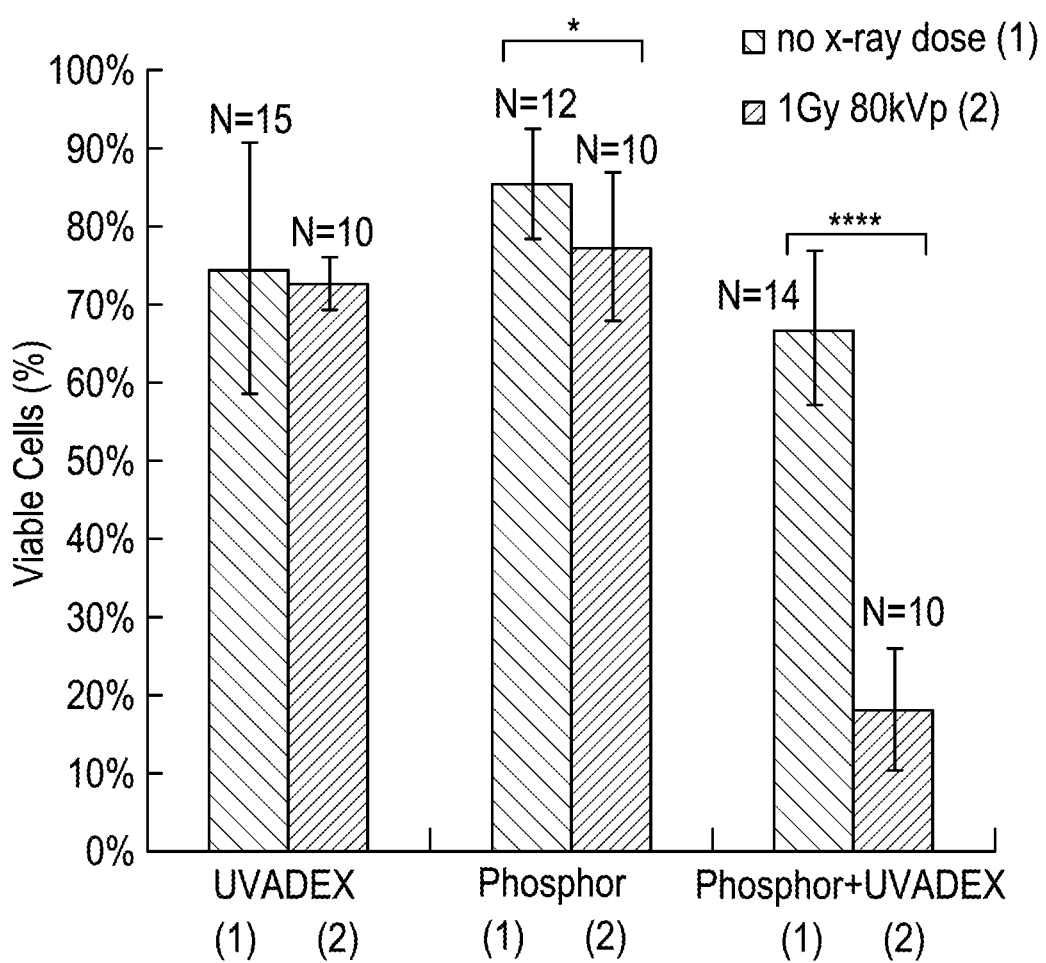
FIGS. 13A, 13B, 13C, and 13D illustrate the efficacy of a treatment in-vitro against 4TI-HER2 cells.
Figure 13B:
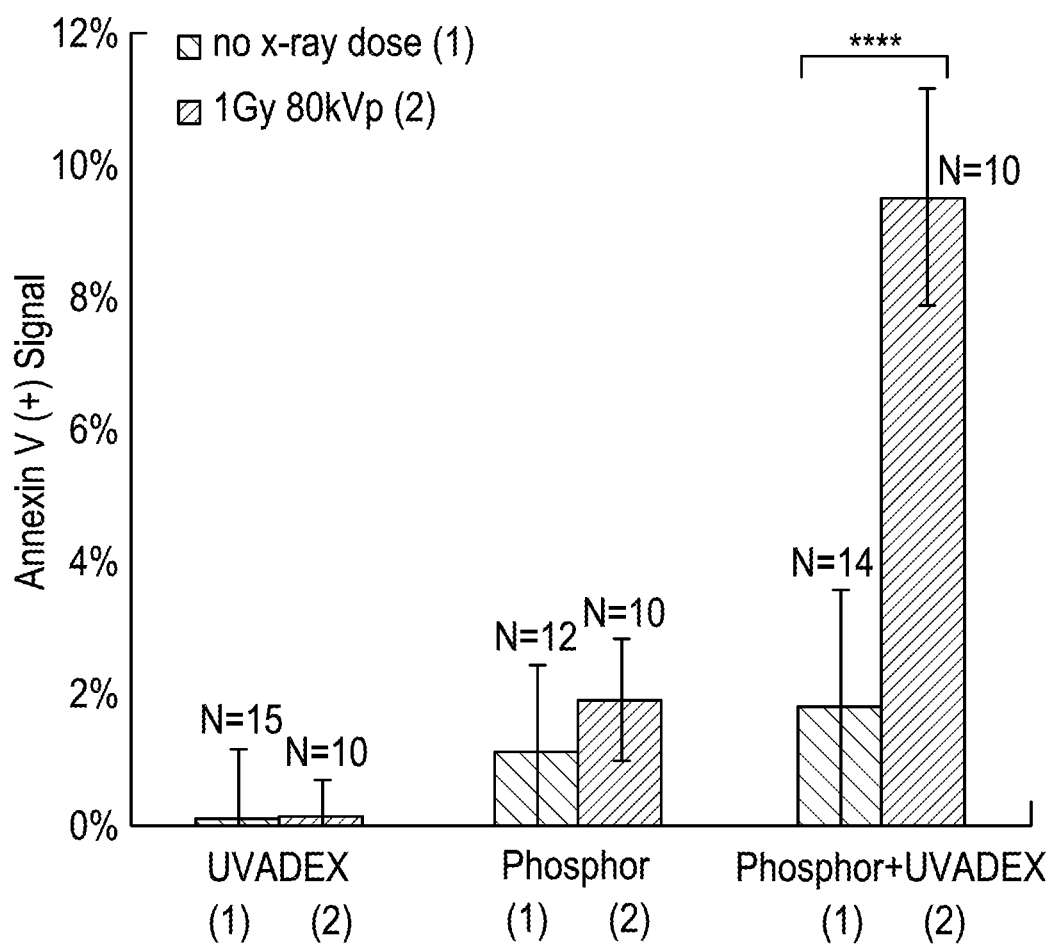
Figure 13C:
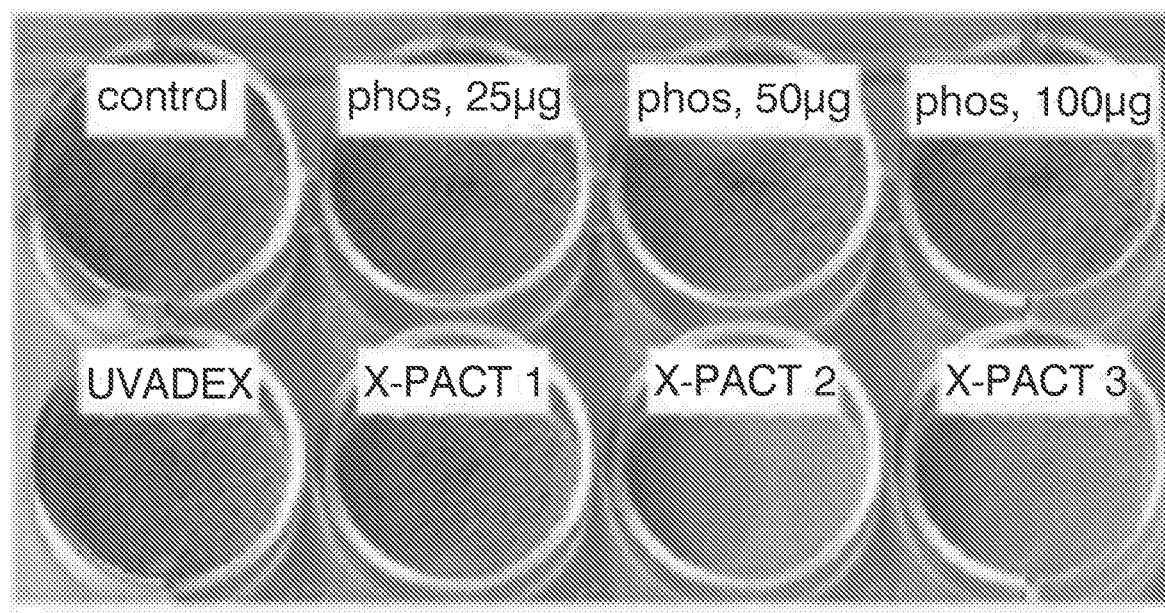
Figure 13D:
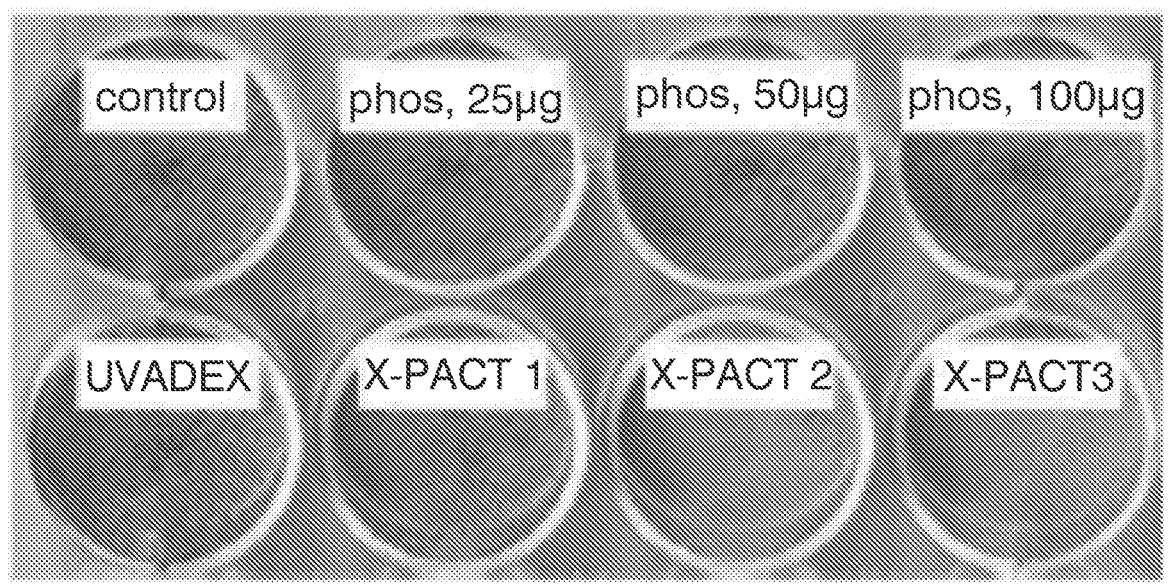
Figure 14A:
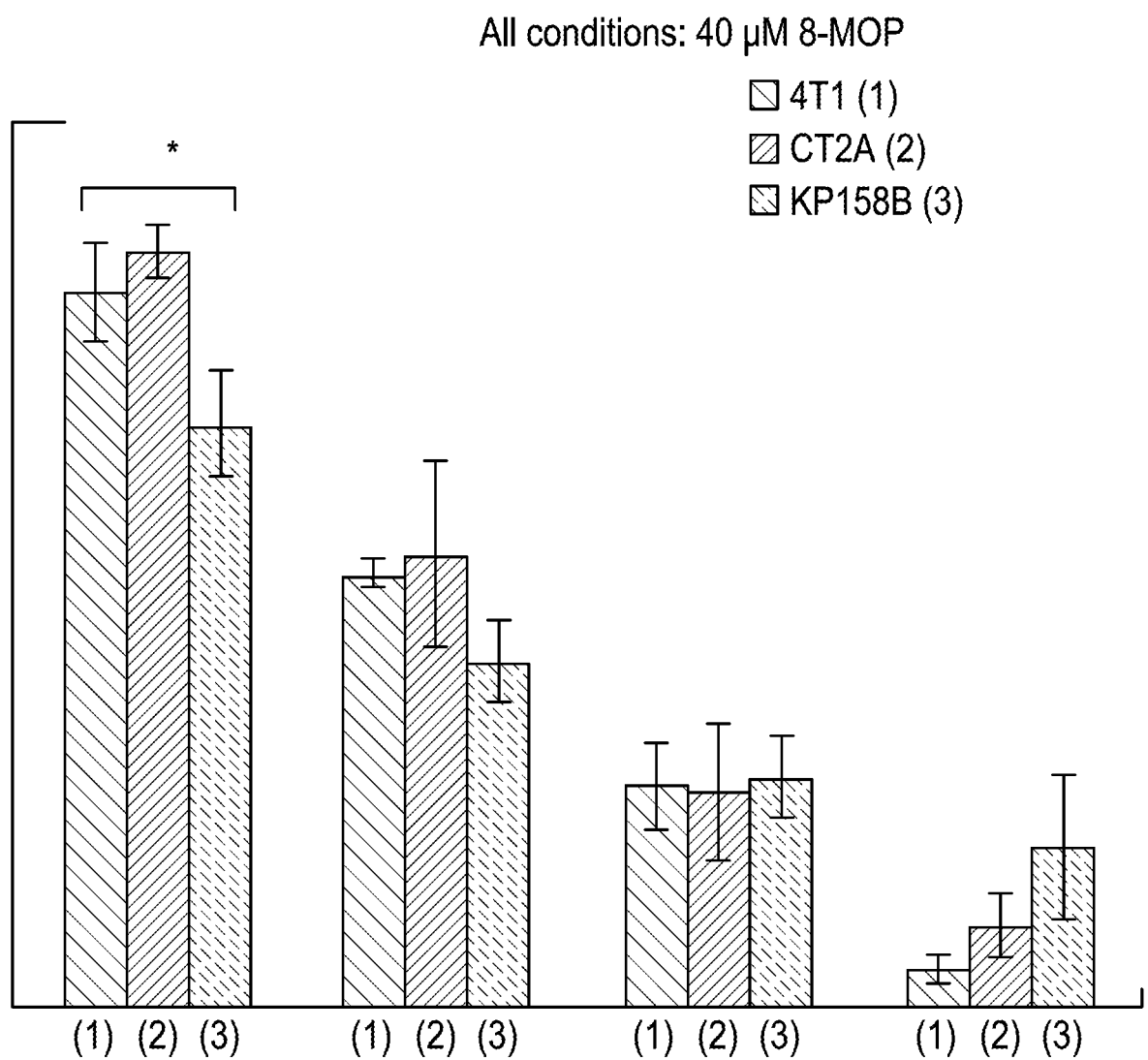
FIGS. 14A and 14B are illustrations of the relative effectiveness of LIV activated psoralen on three independent cell lines.
Figure 14B:
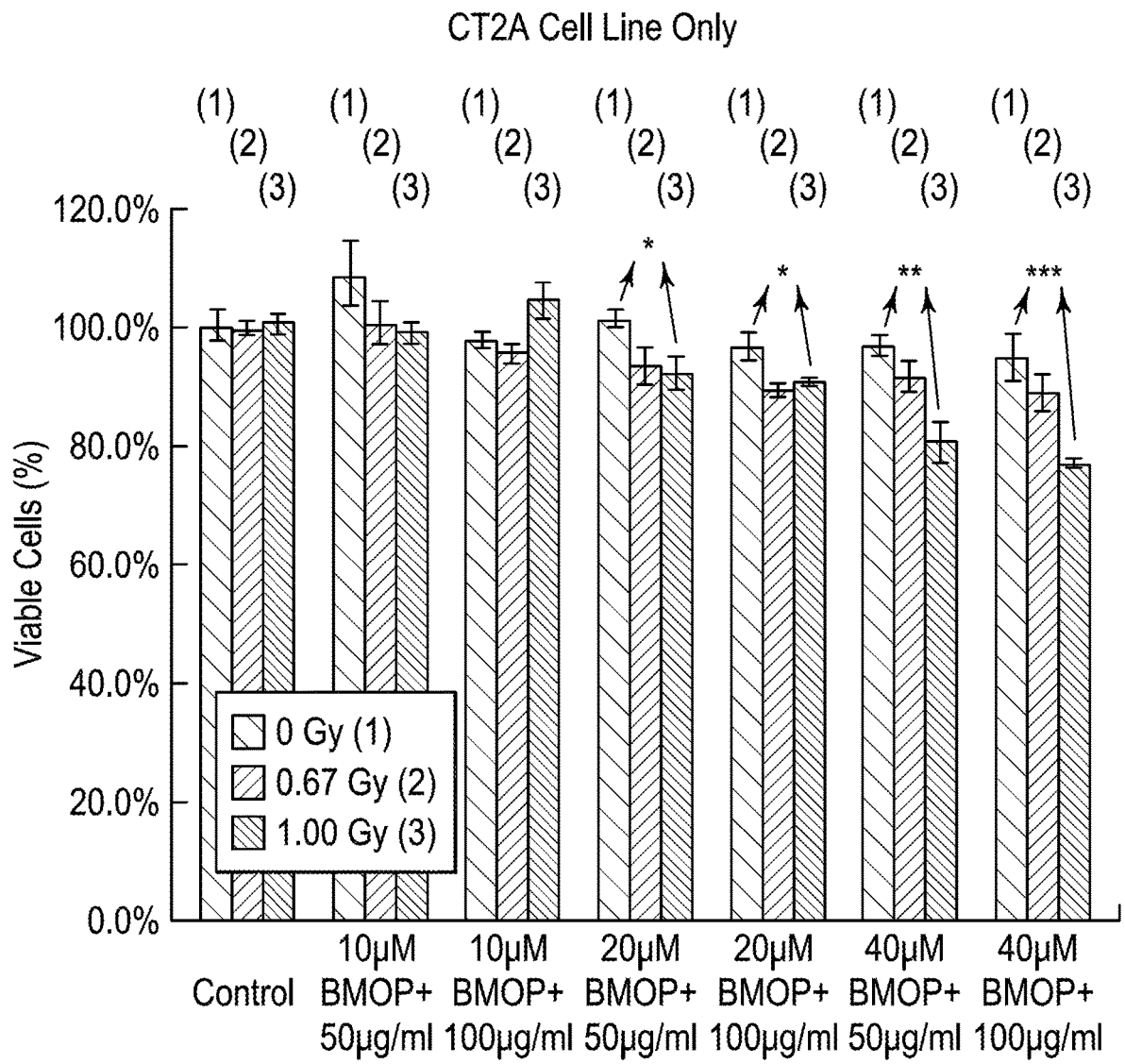

FIGS. 13A-13D illustrates the efficacy of treatment in-vitro in 4T1-HER2 cells, utilizing a regimen of ¹⁄₁₀-diluted UVADEX (with equivalent of 10 uM 8-MOP), 50 µg/mL phosphor 1 Gy of 80 kVp x-rays. FIG. 13A presents the cell viability data for three treatment conditions: UVADEX alone, phosphors alone, and the combination of UVADEX and phosphors. These data were compiled from experiments performed on 5 different days (within 1 month), including 15 separate experimental and 10 control plate irradiations. FIG. 13B presents the Annexin V (+) signal for the same 3 conditions as FIG. 13A. FIGS. 13C and 13D show corresponding images of viable cell populations revealed by methylene blue staining. Two results from two separate plates are shown, each with identical preparations to investigate reproducibility. Three concentrations of phosphor (25, 50, & 100 µg/mL) were tested with the UVADEX concentration fixed at ¹⁄₁₀ dilution (10 uM 8-MOP). The anti-tumor effect is evident from this data. In FIGS. 13A-13D, the anti-tumor effects of the treatment and its individual components on 4T1-HER2 cells. In FIG. 13A, cell viability after treatment (10 µM 8-MOP equivalent dilution of UVADEX, 50 µg/mL phosphor, 1 Gy of 80 kVp radiation) as determined by Guava flow cytome cytometry is depicted. N is the number of independent measurements (different days), and error bars indicate one standard deviation. In FIG. 13B, the Annexin V (+) fraction of viable cells shown in 13A. In FIGS. 13C and 13D, cell viability illustrated by methyl blue staining for identical plates each receiving 1 Gy of 80 kVp x-rays is depicted. Each plate contained wells including no additives (control), three concentrations of phosphor only (25, 50, & 100 μg/mL. with DLC), UVADEX only (10 uM 8-MOP equivalent dilution), and three combination treatment regimes The relative effectiveness of UV activated psoralen on the three independent cell lines noted above is shown in FIGS. 14A and 14B. FIG. 14A shows comparable sensitivity of CT2A (murine malignant glioma), 4T1 and KP-B (sarcoma) cell lines to psoralen activated by the phosphor device. FIG. 14B presents data on CT2A malignant glioma cells, for a range of treatment parameters including variable x-ray dose (0, 0.67 and 1 Gy). phosphor concentration (50 or 100 μg) and psoralen concentration (8-MOP) at 10, 20 and 40 μM respectively. For FIG. 14A, x-ray induced UV light activated psoralen was observed to reduce viable cells in 3 cell lines (data from Cell-Titer-Glo® Luminescence Cell Viability Assay under x-ray induced UV light). N=4 for each cell line at each UV light condition (0, 0.25, 0.5, 1.0 J/cm2). The psoralen concentration was 40 μM. For FIG. 14B, in CT2A cells, the treatment cytotoxicity increases with X-ray dose (0, 0.67 and 1.00 Gy respectively), concentration of 8-MOP psoralen (10, 20 and 40 μM respectively), and phosphor (50 and 100 μg/ml) respectively (p values shown thereon).

Figures 15A, 15B:
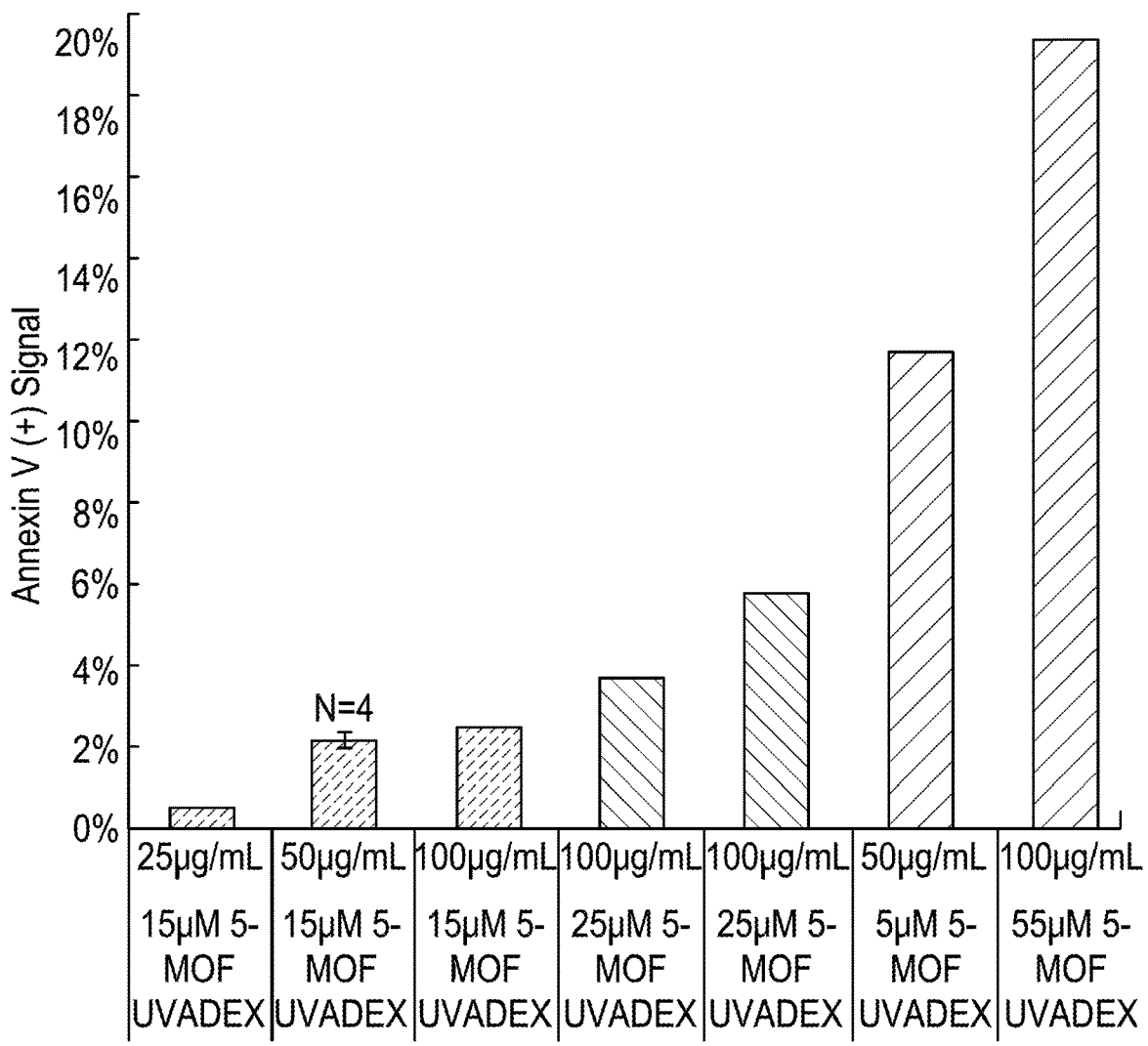
FIGS. 15A and 15B are illustrations of the anti-tumor effects of the x-ray psoralen activated cancer therapy (XPACT) treatment and individual components on 4T1-HER2 cells.

FIG. 15A presents a multi-variable linear regression analysis on thirty-six (36) independent measurements (wells) of Annexin V (±) as a function of two variables: psoralen concentration, and phosphor concentration. Psoralen and phosphor concentrations ranged front 10 μM to 50 μM and 25 μg/mL to 200 μg/mL, respectively. Each of the 36 wells was irradiated with 1 Gy of x-ray radiation at 80 kVp. The fit had the following form given in Equation 1 (where P=phosphor, and Conc=concentration):

$$\text{Annexin } V(+) = A + B^*[\text{8-MOP Conc}] + C^*[P \text{ Conc}] + D^*[\text{8-MOP Conc.}]^*[P \text{ Conc.}] \quad \text{Eq 1}$$

For FIG. 15A, a multi-variable linear regression analysis on thirty-six (36) independent measurements of Annexin V (+) in 4T1-Her2 cells as a function of psoralen and phosphor concentration. All samples received an x-ray dose of 1 Gy at 80 kVp. Psoralen and phosphor concentrations ranged from 10 μM to 50 μM and from 25 μg to 200 mg respectively. The filling equation is given at the top of the Table and in Equation 1. The overall fit was statistically significant as were each of the fit coefficients. FIG. 15B shows a subset of data collected which demonstrate the magnitudes and effects of increasing concentrations of psoralen and phosphor on Annexin V (+) staining. For FIG. 15B, a subset of the data that was collected on a single day, indicating magnitude and trends. Neat UVADEX 8-MOP) was diluted to 10, 20. and 50 μM, or 1:10, 1:5, and 1:2 UVADEX. Four repeats (N=4) were performed for the condition with 50 μg/mL of phosphor and 10 μM of 8-MOP diluted from UVADEX.

Figure 16:
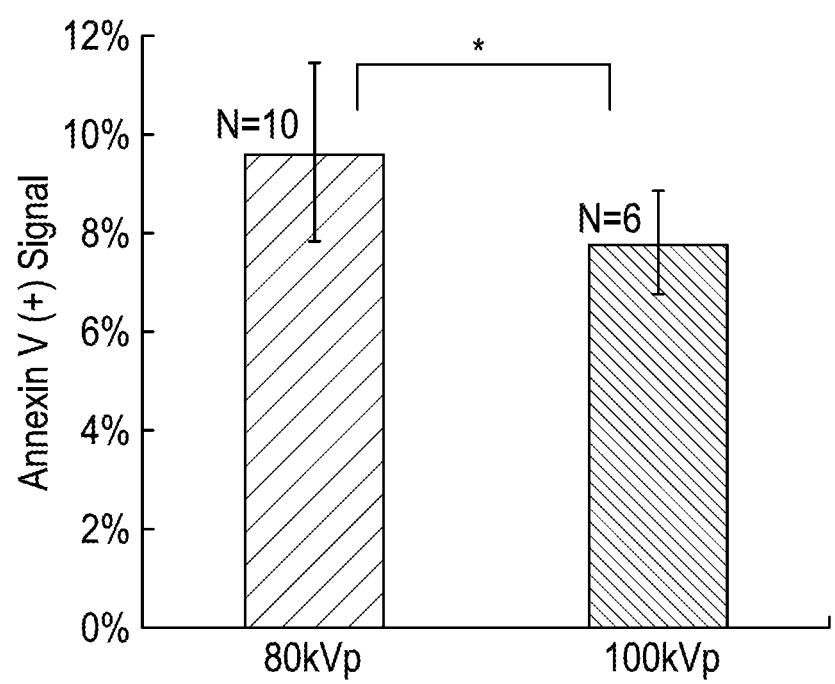
FIG. 16 is a comparison of the phosphor-containing drug activator at two different x-ray energies (80 and 100 kVp) for 4T1-HER2 cells treated with 8-MOP.

FIG. 16 compares the use of the phosphor-containing drug activator at two different x-ray energies (80 and 100 kVp). These experiments involved 4T1-HER2 cells treated with 10 μM 8-MOP equivalent UVADEX, and 50 μg/mL phosphors. Specifically, in FIG. 16, a treatment effect in 4T1-her2 was observed at both 80 and 100 kVp, with suggestion that 80 kVp may be slightly more effective than 100 kVp (p=0.011, *). This data acquired from X-PACT treatment of 4T1-HER2 cells with constant phosphor concentration of 50 μg/mL and UVADEX diluted to 8-MOP concentration of 10 μM (1:10 dilution). N is the number of independent measurements.

Discussion of Murine Studies

In the 4T1 in-vitro cell viability analysis (FIG. 13A), a substantial reduction in viable cells (~48%, p<0001) was observed in the full treatment condition (phosphor device. psoralen, and x-ray). Cell viability was higher (70-85%) in the control conditions.

The effect of adding radiation to the control conditions did not lead to a reduction in cell viability. The addition of radiation to UVADEX alone (left bars in FIG. 13A) had no significant effect on cell viability (p=0.97). Cells exposed to phosphors alone (middle bars in FIG. 13A) show a slight reduction in cell viability (~8%, p=0.034) when radiation was added. The increased toxicity associated with the presence of both phosphors and x-rays could be attributed to DNA damage arising by UV light from x-ray induced phosphorescence from the phosphors. Substantial cytotoxicity (~80%) was only observed in the full treatment arm, demonstrating the synergistic therapeutic effect of the combination of phosphor, UVADEX and radiation.

In the 4T1 in-vitro apoptotic analysis (FIG. 13B), cells exposed to UVADEX alone (left bars) exhibited negligible apoptotic activity either with or without x-ray (p values of 0.90 and 0.09 respectively). There was a slight increase in Annexin V staining when cells were exposed to phosphor alone (middle bars) (~1%, p=0.098) suggesting a slight toxicity of the phosphors. However, it was only when both phosphor and UVADEX were combined (right bars) that a statistically significant increase in Annexin V staining was observed (~8%, p<0.0001), indicating an increase in apoptosis. The anti-tumor effects of the treatment were further illustrated in the methyl blue staining in FIGS. 13C and 13D. In both treatments, little effect was observed for the individual components of UVADEX and phosphor. The methyl blue staining results are consistent with the flow cytometry data, in that all treatment components are required for high cytotoxicity. Less cytotoxicity is manifest in the first treatment condition because of decreased phosphor concentration.

When evaluated on the three different cell lines (FIG. 14A), an ANOVA analyses reveals no statistically significant differences in the sensitivity of these lines either to individual components or to full treatment (p>0.05). This observation suggests that treatment may have applicability to a range of different tumor types. In CT2A malignant glioma cells, cell cytotoxicity was observed (FIG. 14B) to increase with the magnitude of X-ray dose (0, 0.66 and 1 Gy respectively), concentration of 8-MOP psoralen (10, 20 and 40 μM respectively), and phosphor (50 and 100 μg/ml respectively). Two-sample unequal variance t-test analyses revealed that the effect of 1 Gy radiation was significant on CT2A cells for 20 μM 8-MOP+50 μg/mL phosphors and larger concentrations, but was not significant below those concentrations, especially for the control group. This suggests that radiation itself is not the cause of the increased cytotoxicity.

The most comprehensive in-vitro 4T1 analysis (FIG. 15A) revealed a statistically significant multi-variable linear regression (R2=0.72), The synergy interaction coefficient D was statistically significant (p<0.0001) and positive indicating an enhanced effect when phosphor and psoralen were present. The interaction coefficients for psoralen and phosphor alone were only weakly suggestive (p~0.1 and 0.05 respectively). The p values indicate likely significance, hut gave no indication of magnitude of effect, which is shown in FIG. 15B. A general observation from this data, acquired with constant x-ray dose, is that apoptotic fraction induced by the treatment increases with either increasing phosphor or psoralen concentration.

In FIG. 16, the in-vitro study investigated whether changing x-ray energy had much effect on the treatment efficacy.

This study indicated that ~80 kVp would be optimal, but a higher energy would have an advantage from treatment delivery perspective (greater penetration in tissue). For this reason a 100 kVp beam energy was investigated. An increase in apoptotic signal (over the control) was observed for treatments at both energies.

Canine Study

A pilot study of spontaneous tumors in canine companion animals was conducted. The primary endpoint was device safety, with secondary endpoints to include treatment feasibility and tumor response. Each of six dogs was treated three times a week for three consecutive weeks. The treatment consisted of anesthetizing the dog, administering the phosphor-containing drug activator in a slurry of UVADEX and delivering 0.6 to 1 Gy of 80 kVp x-ray energy from a cone beam CT system. Dogs were followed for one year post treatment.

The following protocols were utilized in the canine study.

Protocol Summary: Without limiting the invention, the following describes nine (9) repeated sessions including tumor measurements, visualizations, and treatments. (More or less than nine sessions can be used depending on the state of the malignancy. Indeed, a treatment with 3-5 sessions might be useful in situations where the tumor is near surface and thorough exposure of the tumor is likely at each session. Alternatively, a treatment with 12-15 sessions might useful in situations where the tumor is within a human organ inside the musculoskeletal system exposure of the tumor is limited to the radiation exposure dose. Moreover, while described below with emphasis on canine treatments, the invention is not limited to the use of these protocols to canines as other animal and human patients could benefit.)

While other measurements, evaluations, and treatments for the malignancies can occur, each session typically included: tumor measurements, toxicity scoring, labwork (collected-at treatments #2, 3, 6 and 9), intratumoral injections of drug and energy modulator substances (preferably while anesthetized), and radiation treatment (RT) with for example radiation of 1 Gy via 80 kVp X-rays. Following the nine sessions, there were follow-up weekly evaluations 3 and 6 weeks after completing the last RT. The follow-up weekly evaluations a) evaluated acute local and systemic toxicity via physical examination and routine labwork, and b) estimated the tumor volume. Following the nine sessions, there were follow-up monthly evaluations at 3, 6, 9 and 12 months after completing the last RT. The follow-up monthly evaluations a) evaluated delayed local toxicity via physical examination, and b) described duration of local tumor in enrolled cases.

Treatment and Imaging: As noted above, subjects in the protocol were anesthetized nine (9) times over 3 weeks. The treatment included intratumoral injections of a slurry containing the novel phosphor-containing drug activator described above. During the radiation treatment, the tumor is imaged preferably using a cone-beam CT technology. The imaging may provide an indication of the localization of phosphors and there distribution throughout the volume of the tumor.

Intratumoral Injections:
1. 3-dimensional caliper measurements of the tumor.
2. Tumor volume will be estimated by multiplying the product of 3 orthogonal diameters by π/6.
3. The total volume to be injected into each tumor follows the regiment outlined below using vials of sterilized phosphor to be mixed UVADEX™ (100 μg/mL 8-MOP) as the sole diluent

TABLE 11

| Tumor volume | mL of slurry per cm$^3$ tumor | | milligrams of phosphor per cm$^3$ of tumor | | Total volume injected |
|---|---|---|---|---|---|
| | Min | Max | Min | Max | |
| 8-15 cubic centimeters | 0.034 | 0.063 | 0.333 | 0.625 | 0.5 mL |
| 15-29.9 cubic centimeters | 0.033 | 0.067 | 0.334 | 0.667 | 1 mL |
| 30-49.9 cubic centimeters | 0.040 | 0.067 | 0.401 | 0.67 | 2 mL |
| 50-74.9 cubic centimeters | 0.040 | 0.060 | 0.401 | 0.600 | 3 mL |
| 75-99.9 cubic centimeters | 0.040 | 0.053 | 0.400 | 0.533 | 4 mL |
| >100 cubic centimeters | 0.044 | 0.050 | 0.435 | 0.500 | 5 mL |

Especially for the canine treatments, but also for other patients, the fur/hair was clipped to improve visibility of the tumor. The tumor skin overlying the tumor was prepared via three (3) alternating scrubs of alcohol (or sterile saline) and chlorohexidine (or iodine).

A grid (e.g., of 1 cm squares) can optionally be used to ensure distribution of the phosphor injections over the course of multiple treatments. Each week, typically, the center and corners can be marked (e.g., with a permanent or paint marker) in blue at the first of that week's treatments, green at the second treatment and white at the 3rd treatment The grid can serve as a template for free-hand injection of the psoralen/phosphor slurry. The grid can be rotated (in the same plane, pivoting about the center) 0.25 cm per day.

An appropriate amount of individual, coated phosphors were weighed into a glass crimp top vial, fitted with a Teflon septum top and an aluminum crimp ring, sealed via a crimp tool and autoclaved on a dry goods cycle (250° C., 30 minutes) and immediately removed from the autoclave, allowing to cool to room temperature. The sterilized materials were stored at room temperature, protected from light until use.

In one example, approximately 30 minutes prior to injection, sterilized phosphors in sealed, crimp top vials were rehydrated with the indicated volume of UVADEX via a sterile needle through a septum cap. Post addition of UVADEX, the entire mixture was continuously vortexed (using a laboratory grade vortex mixer set to the highest setting) for approximately 2 minutes. The mixed sample was introduced into a sterile syringe and sealed with a luer lok cap. Syringes were delivered to the treatment room and immediately prior to intratumoral injection, the sealed syringed was mixed via vortex for approximately 30 sec followed by injection into the desired subject site.

A 20-25 gauge sterile hypodermic needle was used to make free-hand injections in multiple injection sites across the tumor, or at the corner of each square on the grid (if used). (Changing the size of the needle or syringe can be used to optimize the injection distribution.) The total volume to be injected was divided evenly. Injections were preferably made into palpable tumor, but not adjacent normal tissues. The plunger was depressed as the needle was withdrawn from the tumor, to maximize the distribution of phosphors and UVADEX.

In one embodiment, tumors on or near the surface can be palpated to facilitate delivery of the phosphors. Typically, multiple injections are made to help distribute the phosphors throughout the tumor mass. For deeper treatment areas where the tumor cannot be palpated, ultrasound guidance can be employed. Additionally, ultrasound can be used to assist in the dispersion of the UVADEX after the phosphors were delivered to the treatment site.

This protocol used UVADEX (8-methoxypsoralen) as the activatable pharmaceutical agent (using concentrations in the range of 10 μg/mL to 50 μg/ml), and used H100 (diamond coating formed in the presence of 40 atomic % hydrogen) and EC (ethyl cellulose coating) with the combination phosphor being a 1:2 mixture of NP200:GTP-4300.

Following injection of the phosphors and UVADEX, radiation therapy followed immediately.

Radiation Therapy:

0.6-1 Gy of radiation was delivered per treatment session using 80-100 kVp X-rays from the on board imaging (OBI) device of a Novalis Tx radiosurgery platform. (Besides the OBI device of a Varian linear accelerator, a Trilogy, iX, TruBeam, etc. could be used with appropriate adjustment of x-ray dose and energy). With regard to the Novalis Tx platform, this platform includes three imaging modalities for pinpointing a tumor and positioning the patient with high precision. The OBI may be programmed to provide continual imaging during treatment to detect movement and support robotic adjustments in patient positioning in six dimensions (although image quality during treatment will not be optimum). The patient disposed on the Novalis Tx platform is positioned above the concentric imaging position of the x-ray source at a distance of 50 to 70 cm from the x-ray anode.

Subjects can be positioned on a linear accelerator's treatment couch (with the gantry at zero degrees) with the tumor centered at the isocenter of the linear accelerator (centering accomplished using visual inspection and lasers from the linear accelerator); the subject can then be vertically raised to a position with a source to surface distance SSD of 70-90 cm, per the optical distance indicator. This corresponds to a source to surface distance of 50-70 cm when the kilovoltage X-ray source (in the on-board imaging system) is moved to zero degrees for irradiation. Subjects with small body size are elevated on a riser which sits atop the 1 linear accelerator's couch, to facilitate a terminal SSD of 50-70 cm; the goal is always to make the terminal SSD (from the kV source) as close to 50 cm as possible, to minimize treatment times.

Immediately following the final intratwnoral injection of the phosphor device (preferably within several minutes) alignment radiation from the x-ray source (fluoroscopy and/or planar radiographs) confirmed that the source was properly positioned to deliver x-rays to the tumor site by imaging of fiducial markers around the tumor. Then, within several or 5 minutes of the final injection, x-rays from the 80 kVp source pulsing for 800 microsecond pulses was delivered to the target site. In one example, the flux of x-rays was interrupted periodically and restarted until a dose of 0.5 to 1.0 Gy has been delivered in total. As an example, multiple pulses can be used with each pulse is set for 80 kV, 200 mA, 800 milliseconds. The total dose (in Gy) delivered was determined by the number of pulses delivered. The number of pulses delivered to achieve the therapeutic dose was a function of the depth and location of the tumor. Bone mass in the exposure region should be accounted for. For example, a radiation therapy typically was designed for a maximum estimated fractional bone dose of 3 Gy per fraction.

After, this therapeutic radiation treatment (preferably less than 30 minutes, more preferably less than 20 minutes), the region of interest was typically exposed to the kilovoltage radiation using the Varian Novalis OBI (on bard imaging system). At least one rotational kilovoltage CBCT is typically scheduled such that images can be stored for evaluation, Additional beam angles collimated per the recommendations can be used.

Sample Collection

Blood samples are collected via peripheral venipuncture, or from a sampling catheter. Free-catch urine samples are collected for urinalyses.

TABLE 12

| Assay | Fluid | Volume per sample | Number of samples (per dog) | Time of sample collection |
|---|---|---|---|---|
| Complete blood count | Whole blood (in EDTA) | 1 mL | 7 | Baseline, day 3, week 1, 2, 3, 6 and 9 |
| Chemistry profile | Serum | 1 mL | 7 | Baseline, day 3, week 1, 2, 3, 6 and 9 |
| Urinalysis | Urine | 1 mL | 7 | Baseline, day 3, week 1, 2, 3, 6 and 9 |
| PK -Day 1 (psoralen) | Plasma | 0.5 mL | 8 | Baseline, 10, 30 minutes, 1, 1.5, 3, 6 and 12 hours |
| PK -Day 9 (psoralen) | Plasma | O.5 mL | 4 | Baseline, 30 minutes, 1.5 and 6 hours |
| Elemental analysis (phosphor) | Plasma | O.5 mL | 10 | Baseline, 30 minutes, 1.5 hours, 6 hours, 12 hours, 3 days, 1, 3, 6 and 9 weeks |
| Stored sample (for future analyses of immune and/or inflammatory mediators) | Plasma | O.5 mL | 10 | Baseline, 30 minutes, 1.5 hours, 6 hours, 12 hours, 3 days, 1, 3, 6 and 9 weeks |

Pharmacokinetic samples were frozen and stored. The pharmacokinetic study determined whether enough psoralen is absorbed systemically to create a concern regarding systemic exposure and toxicity.

Blood and urine samples for elemental analysis were frozen and stored. Additional plasma samples are collected and stored.

The preceding treatment in one patient was further supplemented with a "booster" treatment, that is, the initial treatment considered a "priming treatment, with an additional treatment used to "boost" the initial treatment response. A "booster treatment" in one embodiment could involve re-injecting the tumor with psoralen (or other photoactivatable drug) and radiating the tumor site again. A "booster treatment" in another embodiment could involve re-injecting the tumor with psoralen (or other photoactivatable drug) and an energy modulation agent and radiating the tumor site again. A "booster treatment" in another embodiment could involve radiating the tumor site again, but at a radiation level considered to be at either a palliative or therapeutic level. The purpose of these "booster" treatments is to activate the immune response initially or originally generated within the patient during the initial treatments.

In one embodiment of the booster treatment, the phosphor concentration was increased to 20 mg/mL, the amount of UVADEX was increased 2-4 times, and the treatment frequency was increased to five (5) treatments in five (5) consecutive days. Furthermore, the timing between the prime (initial treatment sessions such as the nine treatments described above) and the booster treatment was set to allow for an initial humoral or cellular immune response, followed by a period of homeostasis, most typically weeks or months after the initial priming treatment.

Clinical Analysis

Hematology Summary Results

Analyzed using Siemens Advia 120:

The results of the clinical tests showed that the minimum mean cell hemoglobin concentration (MCHC) was statistically significantly less than baseline. Despite statistical significance, all values remain within the reference range, and are of no appreciable clinical significance. The minimum lymphocyte count is statistically significantly less than baseline. The 95% confidence interval of that minimum lymphocyte count is below the lower limit of the reference range. The cause of this post-treatment lymphopenia is not known, nor is it of clinical significance.

Urinalysis Summary Results

There were no statistically significant perturbations in parameters measured via urinalysis. Of note:
- 2/6 dogs developed significant but transiently increased proteinuria (4+ bumin) post-treatment
- 4/6 dogs were noted to have 0-5 fine granular casts after treatment; these persisted at the 6 week follow-up exam in one dog
- 4/6 dogs were noted to have 0-2 hyaline casts after treatment; these persisted at the 6 week follow-up exam in one dog
- 2/6 dogs were noted to have rare bilirubin crystals after treatment; none persisted beyond the 3 week recheck visit
- 4/6 dogs were noted to have rare to moderate triple phosphate crystals; these persisted at the 6 week follow-up visit in 2/6 dogs Normal Tissue Toxicity Summary Results One dog experienced grade I skin toxicity (hyperpigmentation and alopecia); first noted at 3 week recheck; has not resolved.

One dog experienced grade I oral mucosal toxicity (erythema); first noted at 3 month recheck; has not been re-evaluated since then.

Tumor Response Summary Results

Tumor response was evaluated in accordance with the Response Evaluation Criteria In Solid Tumors (RECIST) criteria, below:

Complete response (disappearance of target lesion)

Partial response (at least 30% decrease in longest measured dimension, compared with baseline)

Stable disease (neither CR, PR nor PD)

Progressive disease (at least 20% increase in any measured dimension, compared with baseline and most recent measurement)

TABLE 13

Tumor response by RECIST.

| Subject | Response |
| --- | --- |
| #1 | Partial Response at 3 weeks, Complete Response at 6 weeks, 3 months, 6 months, 9 months and 12 months |
| #2 | Stable Disease at 3 weeks, 6 weeks and 3 months. Pursued booster treatment - now a strong Partial Responder 8 months post booster treatment |
| #3 | Stable Disease at 3 weeks, Progressive Disease at 6 weeks, dismissed from study at 3 months and given booster treatment. Elected for surgical removal of tumor |
| #4 | Stable Disease at 3 weeks, 6 weeks, 3 months, progression at 6 months, dismissed from the study to pursue other treatments. |
| #5 | Stable Disease at 3 weeks, 6 weeks, and 3 months. Progressive Disease at 6 months, dismissed from the study to pursue booster. Elected surgical removal of the tumor. |
| #6 | Stable Disease at 3 weeks, progressive disease at 6 weeks, dismissed from study at 3 months |

Figure 17A:
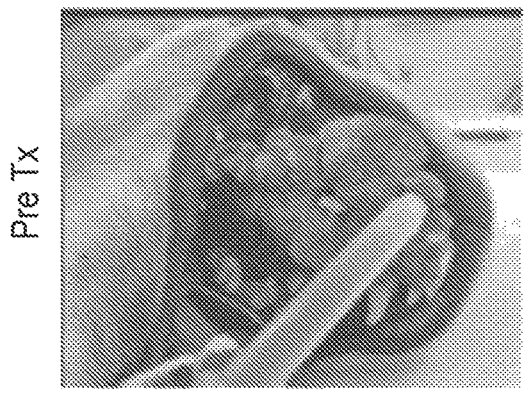
FIGS. 17A and 17B are photographic depictions showing the efficacy of the phosphor-containing drug activator during a canine study pre-treatment and post-treatment on Subject #1, respectively.
Figure 17B:

FIGS. 17A and 17B demonstrate a dramatic and complete response in one subject. The depicted pretreatment photograph (FIG. 17A) is directed to a rostral maxillary tumor with a histopathologic diagnosis of a round cell tumor. The post treatment photograph (FIG. 17B) was taken three weeks after the completion of treatment. This dog remains in complete response one year after treatment.

Figure 18A:
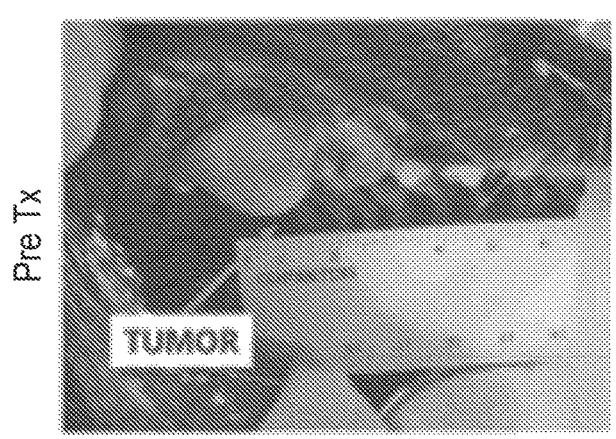
FIGS. 18A and 18B are further photographic depictions showing the efficacy of the phosphor-containing drug activator during the canine study pre-treatment and post-treatment on Subject #2, respectively.
Figure 18B:

FIGS. 18A (pre-treatment) and 18B (post-treatment) depict another dramatic treatment effect. This subject had a maxillary plasma cell tumor with disease progression after melphalan chemotherapy, This dog was treated with the phosphor-containing drug activator and 8-MOP and had stable disease thereafter. An additional "booster" treatment (consisting of 5 treatments in 5 consecutive days) was added, after which the intra-oral part of the tumor completely resolved. The infra-oral component has remained stable for several months.

Variations

In another embodiment, particularly for more aggressive cancers, an intervening treatment between the prime and boost stages can be provided to stunt the growth of the tumor while the immune system develops a response. The intervening treatment can take the form of palliative radiation, or other treatments known to those skilled in the art.

The invention can utilize one or more booster treatments in a manner similar to that described by David L. Woodland in their paper in TRENDS in Immunology Vol. 25 No. 2 February 2004, entitled "Jump-Starting the Immune System: Prime-Boosting Comes of Age" (the entire contents of which are incorporated herein by reference). The basic prime-boost strategy involves priming the immune system to a target antigen, or a plurality of antigens created by the drug and/or radiation induced cell kill, and then selectively boosting this immunity by re-exposing the antigen or plurality of antigens in the boost treatment. One key strength of this strategy in the present invention is that greater levels of immunity are established by heterologous prime-boost than can be attained by a single vaccine administration or homologous boost strategies. For example, the initial priming events elicited by a first exposure to an antigen or a plurality of antigens appear to be imprinted on the immune system. This phenomenon is particularly strong in cells and is exploited in prime-boost strategies to selectively increase the numbers of memory T cells specific for a shared antigen in the prime and boost vaccines. As described in the literature, these increased numbers of T cells 'push' the cellular immune response over certain thresholds that are required to fight specific pathogens or cells containing tumor specific antigens. Furthermore, the general avidity of the boosted T-cell response is enhanced, which presumably increases the efficacy of the treatment.

Here, in this invention and without limitation as to the details but rather for the purpose of explanation, the initial treatment protocol develops antibodies or cellular immune responses to the psoralen-modified or X-ray modified cancer cells. These "initial" responses can then be stimulated by the occurrence of a large number of newly created psoralen-modified or X-ray modified cancer cells, As such, the patient's immune system would mount a more robust response against the cancer than would be realized in a single treatment series.

In one embodiment of the invention, as noted above, the treatments for the non-adherent or liquid tumors can be given once, or periodically (such as 3 to 5 times a week), or intermittently, such as 3 to 5 times a week, followed by a period of no treatment, typically one to two weeks, followed by another treatment period of 3 to 5 times a week.

Additionally, a prime-boost strategy can be employed, such as is described herein for the treatment of solid tumors. The prime phase can be a single treatment, periodic treatment or intermittent treatment, followed by a period of no treatment, typically 6-12 weeks, followed by a booster treatment. The booster treatment can be the same duration and frequency as the prime treatment, or can be accelerated or shortened.

In one embodiment of the invention, prior to the initial treatment or prior to booster treatments, the immune system of the subject could be further stimulated by injection of a more conventional vaccine such as for example a tetanus vaccine. Prior work by others has shown the efficacy of a tetanus booster to bolster the immune system's attack on the tumor by helping cancer vaccines present in the subject migrate to the lymph nodes, activating an immune response. Here, in this invention, the autovaccines generated internally from the treatments described above could also benefit from this effect.

The invention also has utility in treating non-adherent (liquid) tumors, such as lymphoma. Instead of injecting the phosphors and drug into the solid tumor, the phosphor and drug combination can be injected into a lymph node, preferably the draining lymph node distal to a lymphoma tumor, or any lymph node with disease involvement. Alternatively, treating any area with a lymphoma infiltration is acceptable.

Debris from dead and dying tumor cells would be transported to regional lymph nodes where immune activation would occur and tumor specific immune cells would then recirculate and begin to destroy tumor cells at multiple sites. This killing of tumor cells in the lymph or any organ with a lymphoma infiltrate creates more immune stimuli for activation in the regional lymph nodes and further re-circulation, making repeat treatments beneficial.

In one embodiment of the invention, intervening treatments to control the growth or spread of the lymphoma while the immune system activates can also be added. These treatments can include palliative x-ray, enzyme treatments such as asparginase, chemotherapy, or surgery.

The typical tube voltage for radiography is typically in the range of 60-120 kV. The x-ray beam is then passed through filtration achieved by interposing various metal filters in the x-ray path. The metals that can be used include Aluminum (Al) and Copper (Cu). The filtration of the beam eliminates noise and results in a cleaner output beam, preferentially removing softer photons. This leads to a cleaner spectrum and systems from different vendors would result in having substantially the same output spectrum. After filtration the beam is passed through a collimator. X-ray radiation can be collimated into a fan-shaped beam. The beam is passed through an adjustable aperture. Lead (Pb) plates of about 2 mm in thickness can be used to block the beam and limit the exposure of x-ray to the tumor area.

The 60-120 kV beam can be sufficient to activate the bio-therapeutic agent via the phosphors described in this invention.

In one embodiment, a method in accordance with the present invention utilizes the principle of energy transfer to and among different agents to control delivery and activation of cellular changes by irradiation such that delivery of the desired effect is more intensified, precise, and effective than the conventional techniques. The phosphors noted above represent but one energy modulation agent of the present invention. In general, at least one energy modulation agent can be administered to the subject which adsorbs, intensifies or modifies said initiation energy into an energy that effects a predetermined cellular change in said target structure. The energy modulation agent may be located around, on, or in said target structure. Further, the energy modulation agent can transform a photonic initiation energy into a photonic energy that effects a predetermined change in said target structure. In one embodiment, the energy modulation agent decreases the wavelength of the photonic initiation energy (down convert). In another embodiment, the energy modulation agent can increase the wavelength of the photonic initiation energy (up convert). In a different embodiment the modulation agent is one or more members selected from a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

In one aspect of the invention, a downconverting energy modulation agent can comprise inorganic particulates selected from the group consisting of: metal oxides; metal sulfides; doped metal oxides; and mixed metal chalcogenides. In one aspect of the invention, the downconverting material can comprise at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, LuPO$_4$, YVO$_4$, YbF$_3$, YF$_3$, Na-doped YbF$_3$, ZnS; ZnSe; MgS; CaS and alkali lead silicate including compositions of SiO$_2$, B$_2$O$_3$, Na$_2$O, K$_2$O, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration.

NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$ or alloys or layers thereof.

In one aspect of the invention, the energy modulation agents can be used singly or in combination with other down converting or up converting materials.

Below is a list of X-ray phosphors which can be used in the present invention along with their corresponding peak emission values.

TABLE 14

| # | Phosphor | Emission Spectrum Peak Emission (nm) | X-ray Absorption | | Microstructure | | Hygroscopic |
|---|---|---|---|---|---|---|---|
| | | | Emiss Eff (%) | Eff (Z) | K-edge (keV) | Specific Gravity | Crystal Structure | |
| 1 | BaFCl:Eu$^{2+}$ | 380 | 13 | 49.3 | 37.38 | 4.7 | Tetragonal | N |
| 2 | BaSO$_4$-:Eu$^{2+}$ | 390 | 6 | 45.5 | 37.38 | 4.5 | Rhombic | N |
| 3 | LaOBr:Tm$^{3+}$ | 360, 460 | 14 | 49.3 | 38.92 | 6.3 | Tetragonal | N |
| 4 | YTaO$_4$ | 337 | | 59.8 | 67.42 | 7.5 | Monolithic | N |
| 5 | YTaO$_4$:Nb (*) | 410 | 11 | 59.8 | 67.42 | 7.5 | Monolithic | N |
| 6 | CaWO$_4$ | 420 | 5 | 61.8 | 69.48 | 6.1 | Tetragonal | N |
| 7 | LaOBr:Tb$^{3+}$ | 420 | 20 | 49.3 | 38.92 | 6.3 | Tetragonal | N |
| 8 | Y$_2$O$_2$S:Tb$^{3+}$ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn, Cd)S:Ag | 530 | 19 | 38.4 | 9.66/26.7 | 4.8 | Hexgonal | N |
| 11 | Gd$_2$O$_2$S:Tb$^{3+}$ | 545 | 13 | 59.5 | 50.22 | 7.3 | Hexgonal | N |
| 12 | La$_2$O$_2$S:Tb$^{3+}$ | 545 | 12.5 | 52.6 | 38.92 | 6.5 | Hexgonal | N |

In one aspect of the invention, the downconverting energy modulation agent can comprise materials such as ZnSeS:Cu, Ag, Ce, Tb; CaS: Ce,Sm; La$_2$O$_2$S:Tb; Y$_2$O$_2$S:Tb; Gd$_2$O$_2$S: Pr, Ce, F; LaPO$_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include ZnSe$_x$S$_y$:Cu, Ag, Ce, Tb, where the following x, y values and intermediate values are acceptable: x:y; respectively 0:1; 0.1:0.9; 0.2:0.8; 0.3:0.7; 0.4:0.6; 0.5: 0.5; 0.6:0.4; 0.7:0.3; 0.8:0.2; 0.9:0.1; and 1.0:0.0.

In other aspects of the invention, the downconverting energy modulation agent can be materials such as sodium yttrium fluoride (NaYF$_4$), lanthanum fluoride (LaF$_3$), lanthanum oxysulfide (La$_2$O$_2$S), yttrium oxysulfide (Y$_2$O$_2$S), yttrium fluoride (YF$_3$), yttrium gallate, yttrium aluminum garnet (YAG), gadolinium fluoride (GdF$_3$), barium yttrium fluoride (BaYF$_5$, BaY$_2$F$_8$), gadolinium oxysulfide (Gd$_2$O$_2$S), calcium tungstate (CaWO$_4$), yttrium oxide:terbium (Yt$_2$O$_3$Tb), gadolinium oxysulphide:europium (Gd$_2$O$_2$S:Eu), lanthanum oxysulphide:europium (La$_2$O$_2$S: Eu), and gadolinium oxysulphide:promethium, cerium, fluorine (Gd$_2$O$_2$S:Pr,Ce,F), YPO$_4$:Nd, LaPO$_4$:Pr, (Ca,Mg)SO$_4$: Pb, YBO$_3$:Pr, Y$_2$SiO$_5$:Pr, Y$_2$Si$_2$O$_7$:Pr, SrLi$_2$SiO$_4$:Pr,Na, and CaLi$_2$SiO$_4$:Pr.

In other aspects of the invention, the downconverting energy modulation agent can be near-infrared (NIR) downconversion (DC) phosphors such as KSrPO$_4$:EU$^{2+}$, Pr$^{3+}$, or NaGdF$_4$:Eu or Zr$_2$SiO$_4$:Tb$^{3+}$,Yb$^{3+}$ or β-NaGdF$_4$ co-doped with Ce$^{3+}$ and Tb$^{3+}$ ions or Gd$_2$O$_2$S:Tm or BaYF$_3$:Eu$^{3+}$ or other down converters which emit NIR from visible or UV light exposure (as in a cascade from x-ray to UV to NIR) or which emit NIR directly after x-ray or e-beam exposure.

In one aspect of the invention, an up converting energy modulation agent can be at least one of Y$_2$O$_3$, Y$_2$O$_2$S, Various plastic scintillators, plastic scintillator fibers and related materials are made of polyvinyltoluene or styrene and fluors. These materials could be used in the present invention especially if encapsulated or otherwise chemically isolated from the target structure so not as to be dissolved or otherwise deteriorated by the fluids of the target structure. These and other formulations are commercially available, such as from Saint Gobain Crystals, as BC-414, BC-420, BC-422, or BCF-10.

TABLE 15

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

TABLE 16

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Table 17 shows a wide variety of energy modulation agents which can be used in this invention.

TABLE 17

| Phosphor | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2:Ti+ | 310 | | | | | | N |
| BaF2 | 310 | | | | | | Slightly |
| CsI | 315 | | | | | | N |
| Ca3(PO4)2:Ti+ | 330 | | | | | | N |
| YTaO4 | 337 | 59.8 | 67.42 | | 7.5 | Monolithic | N |
| CsI:Na | 338 | | | | | | Y |
| BaSi2O5:Pb2+ | 350 | | | | | | N |
| Borosilicate | 350 | | | | | | N |
| LaCl3(Ce) | 350 | | | | | | Y |
| SrB4O7F:Eu2+ | 360 | | | | | | N |
| RbBr:Ti+ | 360 | | | | | | ? |
| (Ba, Sr, Mg)3Si2O7:Pb2+ | 370 | | | | | | N |
| YaiO3:Ce3+ | 370 | | | | | | N |
| BAlO3:Ce3+ | 370 | | | | | | N |
| BC-422 | 370 | | | | | Organic | ? |
| BaFCl:Eu2+ | 380 | 13 | 49.3 | 37.38 | 4.7 | Tetragonal | N |
| BaSO4-:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |
| SrMgP2O7:Eu2+ | 394 | | | | | | N |
| BaBr2:Eu2+ | 400 | | | | | | N |
| (Sr, Ba)Al2Si2O8:Eu2+ | 400 | | | | | | N |
| YTaO4:Nb(*) | 410 | 11 | 59.8 | 67.42 | 7.5 | Monolithic | N |
| Y2SiO5:Ce3+ | 410 | | | | | | N |
| CaWO4 | 420 | 5 | 61.8 | 69.48 | 6.1 | Tetragonal | N |
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexagonal | N |
| Lu2SiO5:Ce3+ | 420 | | | | | | N |
| LuI.8Y0.2SiO5:Ce | 420 | | | | | | N |
| Zn5:Ag | 450 | 17 | 26.7 | 9.66 | 3.9 | Hexagonal | N |
| CdWO4 | 475 | | | | | | Slightly |
| Bi4Ge3O12(BGO) | 480 | | | | | | N |
| (Zn, Cd)S:Ag | 530 | 19 | 38.4 | 9.66/26.7 | 4.8 | Hexagonal | N |
| Gd2O2S:TB3+ | 545 | 13 | 59.5 | 50.22 | 7.3 | Hexagonal | N |
| La2O2S:Tb3+ | 545 | 12.5 | 52.6 | 38.92 | 6.5 | Hexagonal | N |
| Y3Al5O12(Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

By selection of one or more of the phosphors noted above (or others known in the art), the present invention permits one to provide in a vicinity of or within a target structure one or more light emitters capable of emitting different wavelengths corresponding to respective biological responses, and permits the activation of one or more biological responses in the target structure depending on at least one or more different wavelengths of light generated internally or provided internally within the subject, wherein the different wavelengths activate the respective biological responses (i.e., selective activation).

Another embodiment to deliver the energy modulation agent-PA drugs involves the use of ferritin and apoferritin compounds. There is increasing interest in ligand-receptor-mediated delivery systems due to their non-immunogenic and site-specific targeting potential to the ligand-specific bio-sites. Platinum anticancer drug have been encapsulated in apoferritin. Ferritin, the principal iron storage molecule in a wide variety of organisms, can also be used as a vehicle for targeted drug delivery. It contains a hollow protein shell, apoferritin, which can contain up to its own weight of hydrous ferric oxide-phosphate as a microcrystalline micelle. The 24 subunits of ferritin assemble automatically to form a hollow protein cage with internal and external diameters of 8 and 12 nm, respectively. Eight hydrophilic channels of about 0.4 nm, formed at the intersections of subunits, penetrate the protein shell and lead to the protein cavity. A variety of species such as gadolinium ($Gd^{3+}$) contrast agents, desferrioxamine B, metal ions, and nanoparticles of iron salts can be accommodated in the cage of apoferritin. Various metals such as iron, nickel, chromium and other materials have been incorporated into apoferritin. Zinc selenide nanoparticles (ZnSe NPs) were synthesized in the cavity of the cage-shaped protein apoferritin by designing a slow chemical reaction system, which employs tetraaininezinc ion and selenourea. The chemical synthesis of ZnSe NPs was realized in a spatially selective manner from an aqueous solution, and. ZnSe cores were formed in almost all apoferritin cavities with little bulk precipitation.

Some of the phosphors used for psoralen activation have a high atomic mass with a high probability of interaction with the X-Ray photons. As a result, the phosphors are also X-Ray contrasting agents. An image can be derived through X-Ray imaging and can be used to pin-point the location of the tumor.

In a further embodiment, methods in accordance with the present invention may further include adding an additive to alleviate treatment side-effects. Exemplary additives may include, but are not limited to, antioxidants, adjuvant, or combinations thereof In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable here for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol. and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated. above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the active compounds (phosphors and UVADEX) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

As shown above, the pharmaceutical compositions can be included in a container, pack, or dispenser together with instructions for administration. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

It will also be understood that the order of administering the different agents is not particularly limited. Thus in some embodiments the activatable pharmaceutical agent may be administered before the phosphors comprising the novel phosphor-containing drug activator, while in other embodiments the phosphors may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

STATEMENTS OF THE INVENTION

The following numbered statements of the invention provide descriptions of different aspects of the invention and are not intended to limit the invention beyond that of the appended claims. While presented in numerical order, the present invention recognized that the features set forth below can be readily combined with each other as part of this invention. Furthermore, the features set forth below can be readily combined with any of the elements of the specification discussed above.

1. A phosphor-containing drug activator, comprising:
an admixture or suspension of two or more phosphors capable of emitting ultraviolet and visible light upon interaction with x-rays;
said two or more phosphors comprising $Zn_2SiO_4:Mn^{2+}$ and $(3Ca_3(PO_4)_2Ca(F, Cl)_2: Sb^{3+}, Mn^{2+})$ at a ratio NP-200:GTP-4300 of from 1:10 to 10:1;
each of said two phosphors having at least one coating selected from the group consisting of an ethylene cellulose coating and a diamond-like carbon coating; and, optionally in the case of the suspension, a pharmaceutically acceptable carrier. As noted above, other phosphors and phosphor combinations and ratios can be used in the present invention.

2. The activator of statement 1, wherein said ratio ranges from 1:5 to 5:1.

3. The activator of statement 1, wherein said ratio ranges from 1:2 to 2:1.

4. The activator of statement 1, wherein said ratio is about 1:2.

5. The activator of statement 1, further comprising 8 MOP.

6. The activator of statement 1, wherein said two or more phosphors have a composition that emits said ultraviolet and visible light at wavelengths which activate 8 MOP.

7. The activator of statement 5, wherein said $Zn_2SiO_4:Mn^{2+}$ phosphor has cathodoluminescent emission peaks at 160 nm, 360 nm, and 525 nm.

8. The activator of statement 5, wherein said $(3Ca_3(PO_4)_2Ca(F, Cl)_2: Sb^{3+}, Mn^2)$ phosphor has a cathodoluminescent emission edge at 400 nm and a cathodoluminescent emission peaks at 570 nm.

9. The activator of statement 1, wherein each of said two or more phosphors has a first coating comprising said ethylene cellulose coating on the phosphor, and a second outer coating comprising said diamond-like carbon coating on said first coating.

10. The activator of statement 1, wherein each of said two or more phosphors has an outer coating of said ethylene cellulose coating.

11. The activator of statement 1, wherein each of said two or more phosphors has an outer coating of said diamond-like carbon coating.

12. The activator of statement 1 wherein said ethylene cellulose coating is present and has a thickness between 10 and 100 nm.

13. The activator of statement 1, wherein said ethylene cellulose coating is present and has a thickness between 30 and 60 nm.

14. The activator of statement 1, wherein said diamond-like carbon coating is present and has a thickness between 50 and 200 nm.

15. The activator of statement 1, wherein said diamond-like carbon coating is present and has a thickness between 75 and 125 nm.

16. The activator of statement 1, wherein said $Zn_2SiO_4:Mn^{2+}$ phosphor has a size between 0.05 and 100 microns.

17. The activator of statement 1 wherein said $Zn_2SiO_4:Mn^{2+}$ phosphor has a size between 0.1 and 50 microns.

18. The activator of statement 1, wherein said $Zn_2SiO_4:Mn^{2+}$ phosphor has a size between 0.5 and 20 microns.

19. The activator of statement 1, wherein said $(3Ca_3(PO_4)2Ca(F, Cl)_2: S^{3+}, Mn^{2+})$ phosphor has a size between 0.05 and 100 microns.

20. The activator of statement 1, wherein said $(3Ca_3(PO_4)2Ca(F, Cl)_2: Sb^{3+}, Mn^{2+})$ phosphor has a size between 0.1 and 50 microns.

21. The activator of statement 1, wherein said $(3Ca_3(PO_4)2Ca(F, Cl)_2: Sb^{3+}, Mn^{2+})$ phosphor has a size between 0.5 and 20 microns.

22. The activator of statement 1, which is a suspension and wherein said two or more phosphors and the pharmaceutically acceptable carrier comprise a sterile solution.

23. The activator of statement 22, wherein a ratio of phosphor weight to volume of the sterile suspension ranges from 1 to 50 mg/mL.

24. The activator of statement 22, wherein a ratio of phosphor weight to volume of the sterile suspension ranges from 5 to 25 mg/mL.

25. The activator of statement 22, wherein a ratio of phosphor weight to volume of the sterile suspension ranges from 8 to 10 mg/mL.

26. The activator of statement 1, wherein the diamond-like carbon coating is present and has a water-droplet contact angle between about 90 and 110°.

27. The activator of statement 1, further comprising an additive providing a therapeutic or diagnostic effect.

28. The activator of statement 27, wherein the additive comprises at least one of an antioxidant, an adjuvant, or a combination thereof.

29. The activator of statement 27, wherein the additive comprises an image contrast agent.

30. The activator of statement 27, wherein the additive comprises a vaccine.

31. A system for treating a disease in a subject in need thereof, comprising:
the activator of one of statements 1-30 or combinations thereof,
a photoactivatable drug comprising 8 MOP;
one or more devices which infuse the photoactivatable drug and the activator including the pharmaceutically acceptable carrier into a diseased site in the subject; and
an x-ray source which is controlled to deliver a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

32. The system of statement 31, wherein the photoactivatable drug is untethered from the two or more phosphors.

33. The system of statement 31, wherein the one or more devices administer the photoactivatable drug in accordance with a volume of the diseased site.

34. The system of statement 31, wherein an amount of the phosphors in the pharmaceutical carrier ranges from 0.1 to 0.66 milligrams of phosphor per $cm^3$ of the volume of the diseased site, and a concentration of the photoactivatable drug in the pharmaceutical carrier ranges from 10 µg/mL to 50 µg/mL.

35. The system of statement 31, wherein the x-ray source is configured to generate x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

36. The system of statement 31, wherein the dose of x-rays comprises an amount to cause an auto-vaccine effect in the human or animal body.

37. The system of statement 31, wherein the x-ray source is controlled during a booster treatment to repeat on a periodic basis a treatment of the diseased site.

38. The system of statement 37, wherein, in the booster treatment, at least one of phosphor concentration, photoactivatable drug concentration, and the radiation dose is increased by a factor of at least two times, five times, or ten times respective initial values.

39. The system of statement 37, wherein the booster treatment produces psoralen-modified cancer cells or X-ray modified cancer cells.

40. The system of statement 37, wherein the booster treatment produces radiation damaged cancer cells.

41. The system of statement 37, wherein a period between booster treatments is delayed according to a tolerance level of the human or animal body for radiation-modified. cells generated during the booster treatment.

42. The system of statement 31, wherein the x-ray source directs x-rays to at least one of a tumor or a malignancy.

43. The system of statement 31, wherein the x-ray source directs x-rays to at least one of a eukaryotic cell, a prokaryotic cell, a subcellular structure, an extracellular structure, a virus or priori, a cellular tissue, a cell membrane, a nuclear membrane, cell nucleus, nucleic acid, mitochondria, ribosome, or other cellular organelle.

44. The system of statement 31, wherein the x-ray source directs x-rays to a diseased site in a pulsed manner having an on and off time.

45. The system of statement 44, wherein the x-ray source directs x-rays to the diseased site such that the on time activates the phosphor and the off time is long enough for decay of phosphor light emission.

46. The system of statement 31, wherein the x-ray source directs x-rays to a tumor or a malignancy in a pulsed manner having an on and off time.

47. The system of statement 46, wherein the x-ray source directs x-rays to the tumor or the malignancy such that the on time activates the phosphor and the off time is long enough for decay of phosphor light emission.

48. The system of statement 31. wherein the x-ray source directs x-rays to the diseased site according to a predetermined radiation protocol such that a predetermined change occurs in the diseased site.

49. The system of statement 48, wherein
said predetermined change comprises at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

50. The system of statement 31, wherein the x-ray source is controlled such that a dose of about 1 Gy is delivered using twenty one x-ray pulses spaced apart by 10 seconds; and, each x-ray pulse of 800 ms is delivered from the x-ray source set at a voltage of 80 kV and an amperage of 200 mA.

51. A method for treating a disease in a subject in need thereof using the system of statement 31, comprising:
infusing the photoactivatable drug, and the activator including the pharmaceutically acceptable carrier into a diseased site in the subject; and
delivering a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

52. The method of statement 51, wherein infusing comprises infusing the photoactivatable drug untethered from the two or more phosphors.

53. The method of statement 51, wherein infusing comprises administering the photoactivatable drug in accordance with a volume of the diseased site.

54. The method of statement 51, wherein
an amount of the phosphors in the pharmaceutical carrier ranges from 0.1 to 0.66 milligrams of phosphor per $cm^3$ of the volume of the diseased site, and
a concentration of the photoactivatable drug in the pharmaceutical carrier ranges from 10 µg/mL to 50 µg/mL.

55. The method of statement 51, wherein delivering comprises generating x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

56. The method of statement 51, wherein delivering comprises providing a dose of x-rays in an amount to cause an auto-vaccine effect in the human or animal body.

57. The method of statement 51, wherein delivering comprises providing a booster treatment Which repeats on a periodic basis a treatment of the diseased site.

58. The method of statement 57, wherein, in the booster treatment, at least one of phosphor concentration, photoactivatable drug concentration, and the radiation dose is increased by a factor of at least two times, five times, or ten times respective initial values.

59. The method of statement 57, wherein the booster treatment produces psoralen-modified cancer cells or X-ray modified cancer cells.

60. The method of statement 57, wherein the booster treatment produces radiation damaged cancer cells.

61. The method of statement 57, wherein a period between booster treatments is delayed according to a tolerance level of the human or animal body for radiation-modified. cells generated during the booster treatment.

62. The method of statement 51, wherein delivering comprises directing x-rays to at least one of a tumor or a malignancy.

63. The method of statement 51, wherein delivering comprises directing x-rays to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

64. The method of statement 51, wherein delivering comprises directing x-rays to a diseased site in a pulsed manner having an on and off time.

65. The method of statement 64, wherein delivering comprises directing x-rays to the diseased site such that the on time activates the phosphor and the off time is long enough for decay of phosphor light emission.

66. The method of statement 51, wherein delivering comprises directing x-rays to a tumor or a malignancy in a pulsed manner having an on and off time.

67. The method of statement 66, wherein delivering comprises directing x-rays to the tumor or the malignancy such that the on time activates the phosphor and the off time is long enough for decay of phosphor light emission.

68. The method of statement 51, wherein delivering comprises directing x-rays to the diseased site according to a predetermined radiation protocol such that a predetermined change occurs in the diseased site.

69. The method of statement 68, wherein
said predetermined change comprises at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

70. The method of statement 51, wherein delivering comprises providing a dose of about 1 Gy using twenty one x-ray pulses spaced apart by 10 seconds and, each x-ray pulse of 800 ms is delivered from an x-ray source set at a voltage of 80 kV and an amperage of 200 mA.

Numerous modifications and variations of the invention are possible in light of the above teachings. It is therefore to be understood that within the scope of the appended claims, the invention may be practiced otherwise than as specifically described herein. All of the publications, references, patents, patent applications, and other documents identified above are incorporated by reference herein in their entirety.

The invention claimed is:

1. A phosphor-containing drug activator, comprising:
   an admixture of two or more phosphors capable of emitting ultraviolet and visible light upon interaction with x-rays;
   said two or more phosphors comprising $Zn_2SiO_4:Mn^{2+}$ and $(3Ca_3(PO_4)_2Ca(F, Cl)_2: Sb^{3+}, Mn^{2+})$ at a ratio $(Zn_2SiO_4:Mn^{2+}):(3Ca_3(PO_4)_2Ca(F, Cl)_2: Sb^{3+}, Mn^{2+}))$ of from 1:10 to 10:1;
   each of said two phosphors having at least one coating selected from the group consisting of an ethyl cellulose coating and a diamond-like carbon coating.

2. The phosphor-containing drug activator of claim 1, wherein said ratio ranges from 1:5 to 5:1.

3. The phosphor-containing drug activator of claim 1, wherein said ratio ranges from 1:2 to 2:1.

4. The phosphor-containing drug activator of claim 1, wherein said ratio is about 1:2.

5. The phosphor-containing drug activator of claim 1, wherein said two or more phosphors have a composition that emits said ultraviolet and visible light at wavelengths which activate 8-methoxypsoralen (8-MOP).

6. The phosphor-containing drug activator of claim 1, wherein said $Zn_2SiO_4:Mn^{2+}$ phosphor has cathodoluminescent emission peaks at 160 nm, 360 nm, and 525 nm.

7. The phosphor-containing drug activator of claim 1, wherein said $(3Ca_3(PO_4)2Ca(F, Cl)_2: Sb^{3+}, Mn^{2+})$ phosphor has a cathodoluminescent emission edge at 400 nm and a cathodoluminescent emission peaks at 570 nm.

8. The phosphor-containing drug activator of claim 1, wherein each of said two or more phosphors has a first coating comprising said ethyl cellulose coating on the phosphor, and a second outer coating comprising said diamond-like carbon coating on said first coating.

9. The phosphor-containing drug activator of claim 1, wherein each of said two or more phosphors has an outer coating of said ethyl cellulose coating.

10. The phosphor-containing drug activator of claim 1, wherein each of said two or more phosphors has an outer coating of said diamond-like carbon coating.

11. The phosphor-containing drug activator of claim 1 wherein said ethyl cellulose coating is present and has a thickness between 10 and 100 nm.

12. The phosphor-containing drug activator of claim 1, wherein said ethyl cellulose coating is present and has a thickness between 30 and 60 nm.

13. The phosphor-containing drug activator of claim 1, wherein said diamond-like carbon coating is present and has a thickness between 50 and 200 nm.

14. The phosphor-containing drug activator of claim 1, wherein said diamond-like carbon coating is present and has a thickness between 75 and 125 nm.

15. The phosphor-containing drug activator of claim 1, wherein said $Zn_2SiO_4:Mn^{2+}$ phosphor has a size between 0.05 and 100 microns.

16. The phosphor-containing drug activator of claim 1, wherein said $Zn_2SiO_4:Mn^{2+}$ phosphor has a size between 0.1 and 50 microns.

17. The phosphor-containing drug activator of claim 1, wherein said $Zn_2SiO_4:Mn^{2+}$ phosphor has a size between 0.5 and 20 microns.

18. The phosphor-containing drug activator of claim 1, wherein said $(3Ca_3(PO_4)2Ca(F, Cl)_2: Sb^{3+}, Mn^{2+})$ phosphor has a size between 0.05 and 100 microns.

19. The phosphor-containing drug activator of claim 1, wherein said $(3Ca_3(PO_4)2Ca(F, Cl)_2: Sb^{3+}, Mn^{2+})$ phosphor has a size between 0.1 and 50 microns.

20. The phosphor-containing drug activator of claim 1, wherein said $(3Ca_3(PO_4)2Ca(F, Cl)_2: Sb^{3}+, Mn^{2}+)$ phosphor has a size between 0.5 and 20 microns.

21. The phosphor-containing drug activator of claim 1, wherein the diamond-like carbon coating is present and has a water-droplet contact angle between about 90 and 110°.

22. A suspension of a phosphor-containing drug activator, comprising:
   two or more phosphors capable of emitting ultraviolet and visible light upon interaction with x-rays;
   said two or more phosphors comprising $Zn_2SiO_4:Mn^{2+}$ and $(3Ca_3(PO_4)_2Ca(F, Cl)_2: Sb^{3+}, Mn^{2+})$ at a ratio $(Zn_2SiO_4:Mn^{2+}):(3Ca_3(PO_4)_2Ca(F, Cl)_2: Sb^{3+}, Mn^{2+}))$ of from 1:10 to 10:1;
   each of said two phosphors having at least one coating selected from the group consisting of an ethyl cellulose coating and a diamond-like carbon coating; and
   a pharmaceutically acceptable carrier.

23. The suspension of claim 22, wherein said ratio ranges from 1:5 to 5:1.

24. The suspension of claim 22, wherein said ratio ranges from 1:2 to 2:1.

25. The suspension of claim 22, wherein said ratio is about 1:2.

26. The suspension of claim 22, further comprising 8-methoxypsoralen (8-MOP).

27. The suspension of claim 22, wherein said two or more phosphors have a composition that emits said ultraviolet and visible light at wavelengths which activate 8-methoxypsoralen (8-MOP).

28. The suspension of claim 22, wherein said $Zn_2SiO_4:Mn^{2+}$ phosphor has cathodoluminescent emission peaks at 160 nm, 360 nm, and 525 nm.

29. The suspension of claim 22, wherein said $(3Ca_3(PO_4)2Ca(F, Cl)_2: Sb^{3+}, Mn^{2+})$ phosphor has a cathodoluminescent emission edge at 400 nm and a cathodoluminescent emission peaks at 570 nm.

30. The suspension of claim 22, wherein each of said two or more phosphors has a first coating comprising said ethyl cellulose coating on the phosphor, and a second outer coating comprising said diamond-like carbon coating on said first coating.

31. The suspension of claim 22, wherein each of said two or more phosphors has an outer coating of said ethyl cellulose coating.

32. The suspension of claim 22, wherein each of said two or more phosphors has an outer coating of said diamond-like carbon coating.

33. The suspension of claim 22, wherein said ethyl cellulose coating is present and has a thickness between 10 and 100 nm.

34. The suspension of claim 22, wherein said ethyl cellulose coating is present and has a thickness between 30 and 60 nm.

35. The suspension of claim 22, wherein said diamond-like carbon coating is present and has a thickness between 50 and 200 nm.

36. The suspension of claim 22, wherein said diamond-like carbon coating is present and has a thickness between 75 and 125 nm.

37. The suspension of claim 22, wherein said $Zn_2SiO_4$:$Mn^{2+}$ phosphor has a size between 0.05 and 100 microns.

38. The suspension of claim 22, wherein said $Zn_2SiO_4$:$Mn^{2+}$ phosphor has a size between 0.1 and 50 microns.

39. The suspension of claim 22, wherein said $Zn_2SiO_4$:$Mn^{2+}$ phosphor has a size between 0.5 and 20 microns.

40. The suspension of claim 22, wherein said $(3Ca_3(PO_4) 2Ca(F, Cl)_2: Sb^{3+}, Mn^{2+})$ phosphor has a size between 0.05 and 100 microns.

41. The suspension of claim 22, wherein said $(3Ca_3(PO_4) 2Ca(F, Cl)_2: Sb^{3+}, Mn^{2+})$ phosphor has a size between 0.1 and 50 microns.

42. The suspension of claim 1, wherein said $(3Ca_3(PO_4) 2Ca(F, Cl)_2: Sb^{3+}, Mn^{2+})$ phosphor has a size between 0.5 and 20 microns.

43. The suspension of claim 22, wherein said two or more phosphors and the pharmaceutically acceptable carrier comprise a sterile solution.

44. The suspension of claim 43, wherein a ratio of phosphor weight to volume of the sterile suspension ranges from 1 to 50 mg/mL.

45. The suspension of claim 43, wherein a ratio of phosphor weight to volume of the sterile suspension ranges from 5 to 25 mg/mL.

46. The suspension of claim 43, wherein a ratio of phosphor weight to volume of the sterile suspension ranges from 8 to 10 mg/mL.

47. The suspension of claim 22, wherein the diamond-like carbon coating is present and has a water-droplet contact angle between about 90 and 110°.

48. The suspension of claim 22, wherein the pharmaceutically acceptable carrier further comprises an additive providing a therapeutic or diagnostic effect.

49. The suspension of claim 48, wherein the additive comprises at least one of an antioxidant, an adjuvant, or a combination thereof.

50. The suspension of claim 48, wherein the additive comprises an image contrast agent.

51. The suspension of claim 48, wherein the additive comprises a vaccine.

52. A system for treating a disease in a subject in need thereof, comprising:
the suspension of claim 22;
a photoactivatable drug comprising 8-methoxypsoralen (8-MOP);
one or more devices which infuse the photoactivatable drug and the suspension including the pharmaceutically acceptable carrier into a diseased site in the subject; and
an x-ray source which is controlled to deliver a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

53. The system of claim 52, wherein the photoactivatable drug is untethered from the two or more phosphors.

54. The system of claim 52, wherein the one or more devices administer the photoactivatable drug in accordance with a volume of the diseased site.

55. The system of claim 52, wherein
an amount of the phosphors in the pharmaceutical carrier ranges from 0.1 to 0.66 milligrams of phosphor per $cm^3$ of the volume of the diseased site, and
a concentration of the photoactivatable drug in the pharmaceutical carrier ranges from 10 µg/mL to 50 µg/mL.

56. The system of claim 52, wherein the x-ray source is configured to generate x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

57. The system of claim 52, wherein the dose of x-rays comprises an amount to cause an auto-vaccine effect in the human or animal body.

58. The system of claim 52, wherein the x-ray source is controlled during a booster treatment to repeat on a periodic basis a treatment of the diseased site.

59. The system of claim 58, wherein, in the booster treatment, at least one of phosphor concentration, photoactivatable drug concentration, and the radiation dose is increased by a factor of at least two times, five times, or ten times respective initial values.

60. The system of claim 58, wherein the booster treatment produces psoralen-modified cancer cells or X-ray modified cancer cells.

61. The system of claim 58, wherein the booster treatment produces radiation damaged cancer cells.

62. The system of claim 58, wherein a period between booster treatments is delayed according to a tolerance level of the human or animal body for radiation-modified cells generated during the booster treatment.

63. The system of claim 52, wherein the x-ray source directs x-rays to at least one of a tumor or a malignancy.

64. The system of claim 52, wherein the x-ray source directs x-rays to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

65. The system of claim 52, wherein the x-ray source directs x-rays to a diseased site in a pulsed manner having an on and off time.

66. The system of claim 65, wherein the x-ray source directs x-rays to the diseased site such that the on time activates the phosphor and the off time is long enough for decay of phosphor light emission.

67. The system of claim 52, wherein the x-ray source directs x-rays to a tumor or a malignancy in a pulsed manner having an on and off time.

68. The system of claim 67, wherein the x-ray source directs x-rays to the tumor or the malignancy such that the on time activates the phosphor and the off time is long enough for decay of phosphor light emission.

69. The system of claim 52, wherein the x-ray source directs x-rays to the diseased site according to a predetermined radiation protocol such that a predetermined change occurs in the diseased site.

70. The system of claim 69, wherein
said predetermined change comprises at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

71. The system of claim 52, wherein the x-ray source is controlled such that a dose of about 1 Gy is delivered using twenty one x-ray pulses spaced apart by 10 seconds; and, each x-ray pulse of 800 ms is delivered from the x-ray source set at a voltage of 80 kV and an amperage of 200 mA.

72. A method for treating a disease in a subject in need thereof using the system of claim 52, comprising:
infusing the 8-methoxypsoralen (8-MOP) and the suspension including the pharmaceutically acceptable carrier into a diseased site in the subject; and
delivering a dose of x-rays to the subject for production of the ultraviolet and visible light inside the subject to activate the photoactivatable drug and induce a persistent therapeutic response, said dose comprising a pulsed sequence of x-rays delivering from 0.5-2 Gy to the tumor.

73. The method of claim 72, wherein infusing comprises infusing the photoactivatable drug untethered from the two or more phosphors.

74. The method of claim 72, wherein infusing comprises administering the photoactivatable drug in accordance with a volume of the diseased site.

75. The method of claim 72, wherein
an amount of the phosphors in the pharmaceutical carrier ranges from 0.1 to 0.66 milligrams of phosphor per cm$^3$ of the volume of the diseased site, and
a concentration of the photoactivatable drug in the pharmaceutical carrier ranges from 10 µg/mL to 50 µg/mL.

76. The method of claim 72, wherein delivering comprises generating x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

77. The method of claim 72, wherein delivering comprises providing a dose of x-rays in an amount to cause an auto-vaccine effect in the human or animal body.

78. The method of claim 72, wherein delivering comprises providing a booster treatment which repeats on a periodic basis a treatment of the diseased site.

79. The method of claim 78, wherein, in the booster treatment, at least one of phosphor concentration, photoactivatable drug concentration, and the radiation dose is increased by a factor of at least two times, five times, or ten times respective initial values.

80. The method of claim 78, wherein the booster treatment produces psoralen-modified cancer cells or X-ray modified cancer cells.

81. The method of claim 78, wherein the booster treatment produces radiation damaged cancer cells.

82. The method of claim 78, wherein a period between booster treatments is delayed according to a tolerance level of the human or animal body for radiation- modified cells generated during the booster treatment.

83. The method of claim 72, wherein delivering comprises directing x-rays to at least one of a tumor or a malignancy.

84. The method of claim 72, wherein delivering comprises directing x-rays to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

85. The method of claim 72, wherein delivering comprises directing x-rays to a diseased site in a pulsed manner having an on and off time.

86. The method of claim 85, wherein delivering comprises directing x-rays to the diseased site such that the on time activates the phosphor and the off time is long enough for decay of phosphor light emission.

87. The method of claim 72, wherein delivering comprises directing x-rays to a tumor or a malignancy in a pulsed manner having an on and off time.

88. The method of claim 87, wherein delivering comprises directing x-rays to the tumor or the malignancy such that the on time activates the phosphor and the off time is long enough for decay of phosphor light emission.

89. The method of claim 72, wherein delivering comprises directing x-rays to the diseased site according to a predetermined radiation protocol such that a predetermined change occurs in the diseased site.

90. The method of claim 89, wherein
said predetermined change comprises at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

91. The method of claim 72, wherein delivering comprises providing a dose of about 1 Gy using twenty one x-ray pulses spaced apart by 10 seconds; and, each x-ray pulse of 800 ms is delivered from an x-ray source set at a voltage of 80 kV and an amperage of 200 mA.

* * * * *

UNITED STATES PATENT AND TRADEMARK OFFICE
CERTIFICATE OF CORRECTION

PATENT NO. : 11,260,129 B2  
APPLICATION NO. : 16/074707  
DATED : March 1, 2022  
INVENTOR(S) : Walder et al.

Page 1 of 3

It is certified that error appears in the above-identified patent and that said Letters Patent is hereby corrected as shown below:

On the Title Page

Column 1, Item (87), in "PCT Pub. No.", Line 1, delete "WO2017/013650" and insert -- WO2017/136504 --, therefor.

In the Specification

In Column 1, Line 42, delete ""ADHESIIVE" and insert -- "ADHESIVE --, therefor.

In Column 1, Line 44, delete "tiled" and insert -- filed --, therefor.

In Column 1, Line 58, delete "tiled" and insert -- filed --, therefor.

In Column 3, Line 30, delete "fir" and insert -- In --, therefor.

In Column 3, Line 56, delete "$Mn^{2°}$" and insert -- $Mn^{2+}$ --, therefor.

In Column 4, Line 8, delete "UV ALEX" and insert -- UVADEX --, therefor.

In Column 5, Line 21, delete "LIV" and insert -- UV --, therefor.

In Column 6, Line 4, insert -- to -- after "situ".

In Column 7, Line 9, delete "X-rays)," and insert -- X-rays). --, therefor.

In Column 7, Line 34, delete "machines," and insert -- machines. --, therefor.

In Column 7, Line 53, delete "5 kVp," and insert -- 5 kVp. --, therefor.

In Column 8, Line 39, delete "DIX" and insert -- DLC --, therefor.

Signed and Sealed this  
Fourth Day of October, 2022

Katherine Kelly Vidal  
*Director of the United States Patent and Trademark Office*

CERTIFICATE OF CORRECTION (continued)
U.S. Pat. No. 11,260,129 B2

In Column 9, Line 10, delete "(DLC" and insert -- (DLC) --, therefor.

In Column 10, Line 25, delete "near-surface," and insert -- near-surface. --, therefor.

In Column 10, Line 39, delete "structure," and insert -- structure. --, therefor.

In Column 13, Line 4, delete "(thy-cycle," and insert -- (dry-cycle, --, therefor.

In Column 13, Line 67, delete "e1RB" and insert -- eIRB --, therefor.

In Column 14, Line 25, delete "intratwnoral" and insert -- intratumoral --, therefor.

In Column 14, Line 44, delete "CBCT s" and insert -- CBCTs --, therefor.

In Column 15, Line 9, delete "9A-9E," and insert -- 9A-9E. --, therefor.

In Column 15, Line 21, delete "(3)." and insert -- (3), --, therefor.

In Column 17, Line 3, delete "LSL-Kral;" and insert -- LSL-Kras; --, therefor.

In Column 17, Line 29, delete "plate," and insert -- plate. --, therefor.

In Column 17, Line 60, insert -- (i.e. -- after "dose".

In Column 17, Line 64, delete "(ESC)." and insert -- (FSC). --, therefor.

In Column 18, Line 18, insert -- V -- after "Annexin".

In Column 18, Line 32, delete "0,001<p<0.01." and insert -- 0.001<p<0.01. --, therefor.

In Column 18, Line 33, delete "0,0001<p<0.001." and insert -- 0.0001<p<0.001. --, therefor.

In Column 19, Line 49, delete "20." and insert -- 20, --, therefor.

In Column 20, Line 60, delete "hut" and insert -- but --, therefor.

In Column 21, Line 37, delete "intraturnoral" and insert -- intratumoral --, therefor.

In Column 24, Line 6, delete "intratwnoral" and insert -- intratumoral --, therefor.

In Column 26, Line 46, delete "chemotherapy," and insert -- chemotherapy. --, therefor.

In Column 28, Line 11, delete "asparginase," and insert -- asparaginase, --, therefor.

In Column 33, Line 61, delete "glycol." and insert -- glycol, --, therefor.

CERTIFICATE OF CORRECTION (continued)
U.S. Pat. No. 11,260,129 B2

In Column 37, Line 23, delete "priori," and insert -- prion, --, therefor.

In Column 37, Line 40, delete "31." and insert -- 31, --, therefor.

In Column 38, Line 25, delete "Which" and insert -- which --, therefor.

In Column 38, Line 40, delete "modified." and insert -- modified --, therefor.

In Column 39, Line 11, delete "seconds" and insert -- seconds; --, therefor.